(12) United States Patent
Novet et al.

(10) Patent No.: US 12,399,203 B2
(45) Date of Patent: Aug. 26, 2025

(54) BRIDGE-BASED IMPEDANCE SENSOR SYSTEM

(71) Applicant: Analog Devices, Inc., Wilmington, MA (US)

(72) Inventors: Isaac Chase Novet, Escondido, CA (US); Steven J. Decker, Sandown, NH (US)

(73) Assignee: ANALOG DEVICES, INC., Wilmington, MA (US)

( * ) Notice: Subject to any disclaimer, the term of this patent is extended or adjusted under 35 U.S.C. 154(b) by 0 days.

(21) Appl. No.: 18/672,591

(22) Filed: May 23, 2024

(65) Prior Publication Data
US 2024/0319242 A1    Sep. 26, 2024

Related U.S. Application Data

(63) Continuation of application No. 17/746,577, filed on May 17, 2022, now Pat. No. 11,994,546, which is a
(Continued)

(51) Int. Cl.
*G01R 27/26* (2006.01)
(52) U.S. Cl.
CPC ..... *G01R 27/2629* (2013.01); *G01R 27/2605* (2013.01)
(58) Field of Classification Search
CPC ............ G01R 27/2629; G01R 27/2605; A61B 5/7267; A61B 5/053; H03K 17/955; H03K 17/9622; H03K 2217/96075
(Continued)

(56) References Cited

U.S. PATENT DOCUMENTS

| 3,761,736 A | 9/1973 | Edge et al. |
| 3,836,828 A | 9/1974 | Siegel |

(Continued)

FOREIGN PATENT DOCUMENTS

| EP | 0050353 A1 | 4/1982 |
| WO | 2006/132960 A1 | 12/2006 |

(Continued)

OTHER PUBLICATIONS

International Search Report and Written Opinion received for PCT Patent Application No. PCT/US2020/060932, mailed on May 10, 2021, 21 pages.

*Primary Examiner* — Giovanni Astacio-Oquendo
(74) *Attorney, Agent, or Firm* — ARENTFOX SCHIFF LLP

(57) ABSTRACT

An impedance sensing circuit includes three impedance elements and a sensing element arranged in a bridge configuration. A first input terminal is coupled to two of the impedance elements to apply a stimulus signal. In a mutual-sensing mode, a second input terminal is coupled to the third impedance element and the sensing impedance element to apply an opposite phase stimulus signal. The impedance sensing circuit may be configured in a self-sensing mode, in which the opposite phase stimulus signal is decoupled from the third impedance element and the sensing impedance element. At least one of the impedance elements is variable and may be adjusted to balance an offset impedance load on the sensing element.

20 Claims, 12 Drawing Sheets

Related U.S. Application Data continuation of application No. PCT/US2020/060932, filed on Nov. 18, 2020.

(60) Provisional application No. 62/936,746, filed on Nov. 18, 2019, provisional application No. 62/936,747, filed on Nov. 18, 2019, provisional application No. 62/936,749, filed on Nov. 18, 2019, provisional application No. 62/936,752, filed on Nov. 18, 2019, provisional application No. 62/936,756, filed on Nov. 18, 2019.

(58) Field of Classification Search
USPC .................................. 324/686, 658, 649, 600
See application file for complete search history.

(56) References Cited

U.S. PATENT DOCUMENTS

| | | | |
|---|---|---|---|
| 4,485,673 A | 12/1984 | Stern | |
| 5,412,327 A | 5/1995 | Meinen | |
| 9,804,213 B2 * | 10/2017 | Reynolds | H03K 17/955 |
| 9,952,267 B2 | 4/2018 | Lee | |
| 2003/0111984 A1 * | 6/2003 | Isham | G01R 31/40 323/271 |
| 2010/0292945 A1 * | 11/2010 | Reynolds | H03K 17/9622 702/65 |
| 2013/0314109 A1 * | 11/2013 | Kremin | H03K 17/9622 324/686 |
| 2017/0024078 A1 * | 1/2017 | Bokma | G06F 3/041 |
| 2017/0086702 A1 | 3/2017 | Kim et al. | |
| 2021/0013852 A1 | 1/2021 | Jan et al. | |
| 2021/0089149 A1 * | 3/2021 | Albright | G06F 3/044 |

FOREIGN PATENT DOCUMENTS

| | | |
|---|---|---|
| WO | 2009/158065 A2 | 12/2009 |
| WO | 2010/111668 A1 | 9/2010 |

* cited by examiner

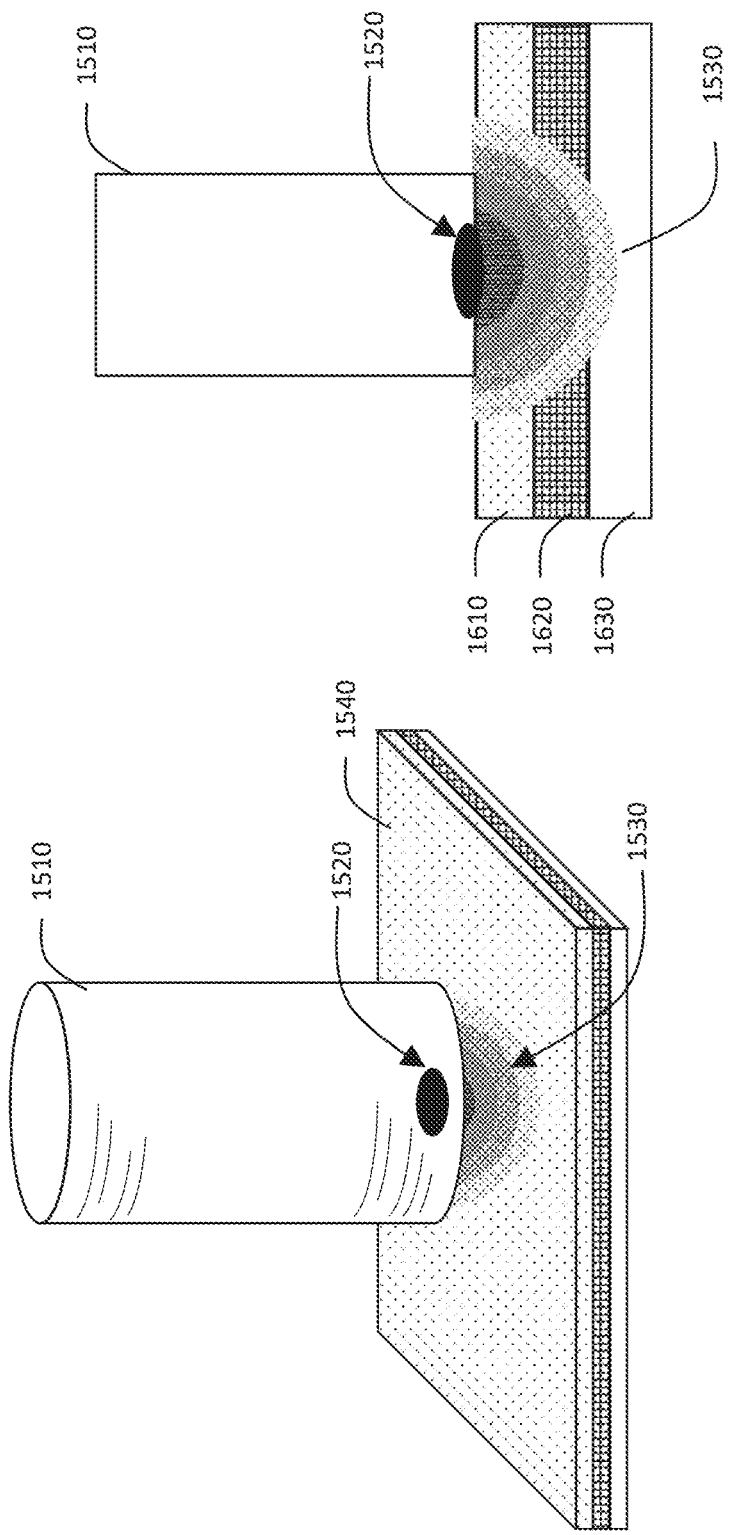

BRIDGE-BASED IMPEDANCE SENSOR SYSTEM

PRIORITY DATA

This application is a continuation of U.S. patent application Ser. No. 17/746,577, filed May 17, 2022, which claims priority to the following International and U.S. provisional patent applications, each of which applications are hereby incorporated by reference herein in their entireties:

International Application No. PCT/US2020/060932, filed Nov. 18, 2020, entitled, "BRIDGE-BASED IMPEDANCE SENSOR SYSTEM"

Application No. 62/936,746, filed Nov. 18, 2019, entitled "SENSING MATERIAL PROPERTIES USING DI-ELECTRIC RELAXATION MEASUREMENTS"

Application No. 62/936,747, filed Nov. 18, 2019, entitled "SENSING ORGANIC TISSUE PROPERTIES USING DI-ELECTRIC RELAXATION MEASUREMENTS"

Application No. 62/936,749, filed Nov. 18, 2019, entitled "SENSING IN-EAR PLACEMENT USING DI-ELECTRIC RELAXATION MEASUREMENTS"

Application No. 62/936,752, filed Nov. 18, 2019, entitled "BRIDGE CAPACITANCE SENSOR"

Application No. 62/936,756, filed Nov. 18, 2019, entitled "SHAPING E-FIELDS FOR DIRECTIONALITY IN DI-ELECTRIC RELAXATION MEASUREMENTS"

TECHNICAL FIELD OF THE DISCLOSURE

The present invention relates to the field of impedance sensors, in particular to a design of a bridge-based impedance sensor system and applications of the impedance sensor system.

BACKGROUND

Capacitance sensing is a common method for detecting the presence or location of an object that is not in physical contact with the sensing device. Current applications of capacitive sensors include gesture sensing, proximity detection, SAR (specific absorption rate) compliance, and material identification.

Existing capacitive sensors generally include one or more electrodes that generate an electric field and measure changes in the electric field caused by objects within the electric field. For example, a capacitive sensor operating in self-sensing mode measures capacitance between an electrode and a ground. When an object is placed near the electrode, the object modifies the electric field between the electrode and the ground and increases the measured capacitance. As another example, a capacitive sensor operating in a mutual-sensing mode has a capacitor formed by two electrodes, with an electric field spanning the electrodes. When a di-electric or metallic object is inserted into the electric field, the capacitance between the two electrodes changes. In the case of a di-electric change between the terminals, the polarization of the di-electric would affect the net capacitance observed between the electrodes. In the case of a metallic change between the electrodes, the introduction of the surface charge distribution between the terminals may modify the electric field distribution, which may change the net capacitance observed between the electrodes.

The offset capacitance between the electrode and ground in self-sensing mode, or between the two electrodes in mutual-sensing mode, can be measured and subtracted from subsequent measurements. This enables sensing of a change in capacitance due to an object near the sensor. In some applications, a device includes multiple capacitive sensors, and spatial and geometric diversity in the placement and sizing of the electrodes may be used to improve signal to noise ratio and to obtain directional observations.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 15 illustrates a speaker with an integrated impedance sensor positioned on a table, according to some embodiments of the present disclosure;

FIG. 16 illustrates a cross-section of the speaker shown in FIG. 15, according to some embodiments of the present disclosure;

DESCRIPTION OF EXAMPLE EMBODIMENTS OF THE DISCLOSURE

Overview

Figure 1:
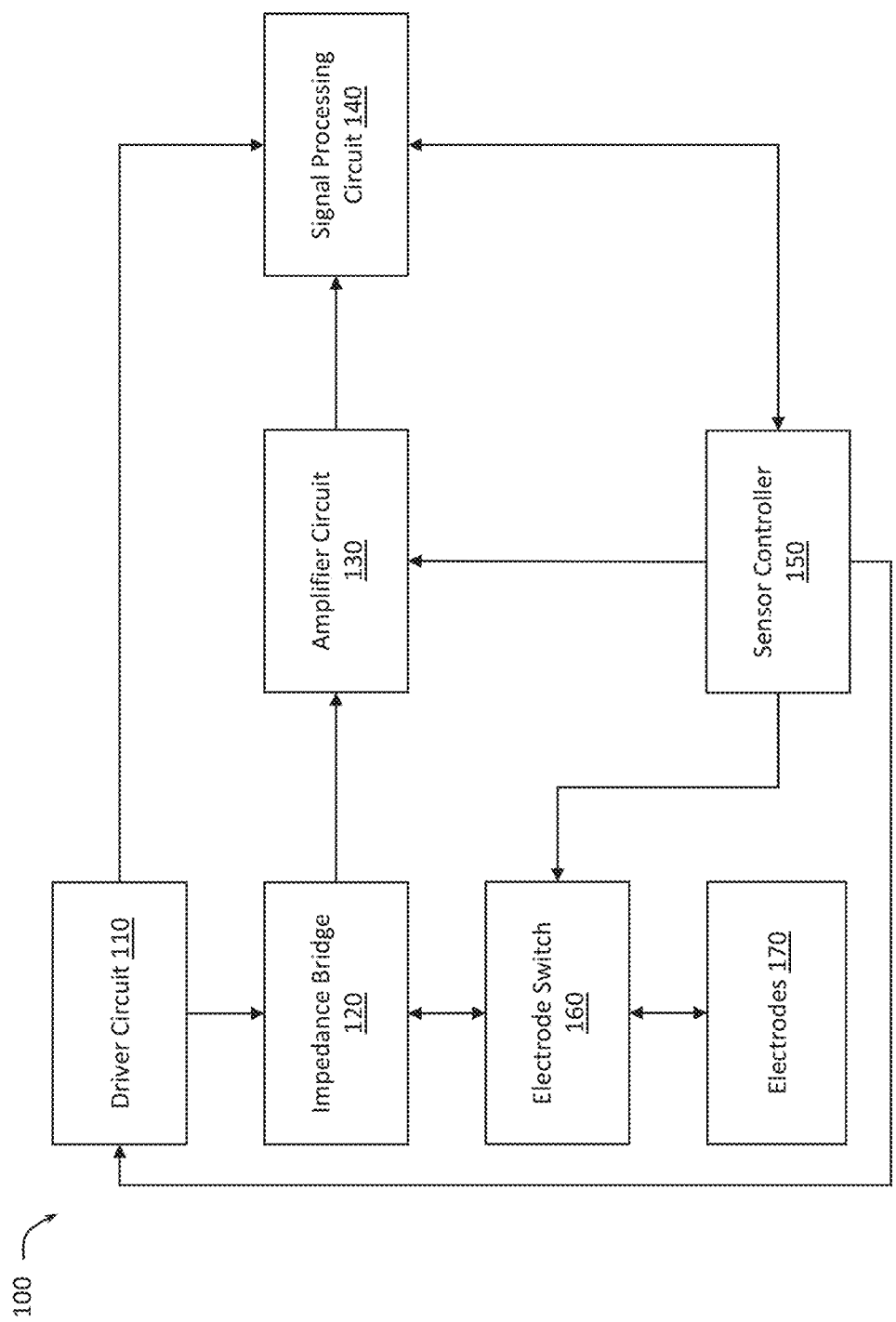
FIG. 1 is a block diagram of a sensor system, according to some embodiments of the present disclosure.

The systems, methods and devices of this disclosure each have several innovative aspects, no single one of which is solely responsible for all of the desirable attributes disclosed herein. Details of one or more implementations of the subject matter described in this specification are set forth in the description below and the accompanying drawings.

In some applications, capacitance sensors are used to sense small changes in a load impedance on top of a fixed impedance. For example, specific absorption rate (SAR) limits for cell phone use require transmit power of the cell phone to be reduced when the cell phone is placed next to a user's head. A capacitance sensor may be used to detect the presence of the head next to the cell phone. The cell phone's antenna creates a large fixed capacitance (e.g., 200 pF) relative to the capacitance change due to the user's head (on the order of 1 fF). Existing capacitance sensors are configured to detect the total capacitance in an environment and subtract the fixed capacitance from the detected total capacitance measurement to determine the change in capacitance due to changes in the field. Such sensors have difficulty detecting such a small change in capacitance in the presence of such a large fixed capacitance.

The sensor system disclosed herein enables measurement of a small change of a load impedance in the presence of a large fixed impedance through the use of an impedance bridge. The impedance bridge has three impedance elements and a coupling network. At least one of the impedance elements is variable, e.g., at least one of the impedance elements includes a variable capacitor and/or variable resistor. The coupling network is couplable to one or more sensing electrodes that generate an electric field and sense an impedance response in the environment of the sensing electrode or electrodes. The impedance bridge is calibrated to account for any fixed impedance in the environment of the electrode(s). The calibrated impedance bridge measures the changes in impedance on top of the fixed impedance, rather than measuring the fixed impedance itself. More particularly, the variable impedance element or elements are set to offset the fixed impedance so that the output of the impedance bridge reflects impedance changes in the environment, while the fixed impedance is cancelled out by the impedance elements.

The impedance bridge has one output terminal between a first and second impedance element. The impedance bridge has another output terminal between the third impedance element and the coupling network. The voltage difference between the two output terminals is related to a change in the impedance sensed by the sensing electrode relative to the fixed impedance. In the SAR example, the impedance elements are calibrated to offset the capacitance of the cell phone's antenna, and the sensor output can be used to determine whether or not the user's head is in the environment of the sensor, i.e., whether there is a change relative to the fixed impedance.

In some embodiments, the sensor can be configured in one of two modes, a self-sensing mode and a mutual-sensing mode, and the sensor can alternate between the self-sensing and mutual-sensing configurations. In the mutual-sensing configuration, the coupling network is coupled to two sensing electrodes, so that one sensing electrode is coupled to an output terminal of the impedance bridge and the other sensing electrode is coupled to an input terminal of the impedance bridge to receive a stimulus signal. A periodic (e.g., sinusoidal) stimulus signal is applied to the input terminal, and a periodic stimulus signal with opposite phase is applied to another input terminal on the opposite side of the impedance bridge. The in-phase and opposite phase (also referred to as antiphase) stimulus signals cancel out at the output terminals of a balanced impedance bridge, so that the output reflects only the impedance change from the offset impedance, and does not reflect the offset impedance itself. In the self-sensing configuration, the coupling network is coupled to one sensing electrode. The sensing electrode is coupled to the output terminal, and a single stimulus signal is applied at the other side of the impedance bridge from the coupling network.

A driver circuit generates the stimulus signal (in the self-sensing mode) or the pair of opposite phase stimulus signals (in the mutual-sensing mode) applied to the impedance bridge. In some embodiments, the driver circuit has an adjustable frequency and can generate different stimulus signals across a range of frequencies. In some examples, a material being sensed may have a frequency-dependent impedance response, and exciting the material at multiple frequencies can help determine the material type. More specifically, the relationship between loss tangent and frequency may be used to identify the material type. In some examples, a frequency is selected to reduce noise in the sensor output signal from other electronics.

The sensor is referred to herein generally as an impedance sensor. In some embodiments, the sensor is used to measure changes in capacitance. The impedance elements may be capacitors, resistors, or a combination of capacitors and resistors. For example, each impedance element may include a variable capacitor and a variable resistor connected in series. In some embodiments, one or more of the impedance elements has a fixed capacitance and/or fixed resistance. In some embodiments, one or more of the impedance elements may be configurable, e.g., in a capacitor bridge configuration and in a resistor pullup configuration. In some embodiments, additional grounded electrodes are used to shape the electric field generated by the sensing electrodes to focus the sensing in a particular region relative to the sensor.

Various applications of the impedance sensor are described herein. An impedance sensor may be integrated into an earphone to detect whether or not the earphone is placed in a user's ear; the earphone may adjust its behavior (e.g., turning off or on) based on its position. In some examples, the impedance sensor is used to determine relative permittivity and/or a frequency-based permittivity response of a material or set of materials around the impedance sensor. As one example, the sensor may be integrated into other devices, such as speakers, to detect materials near the devices, such as the material on which the speaker is sitting. As another example, the impedance sensor may be used as a tissue sensor to identify a type of tissue or to distinguish cancerous tissues from non-cancerous tissues.

Embodiments of the present disclosure provide a sensing circuit that includes an input terminal; a first impedance element coupled between the input terminal and a first output terminal, where the first impedance element is a variable impedance element; a second impedance element coupled between the input terminal and a second output terminal; a third impedance element coupled to the second output terminal; a coupling network coupled to the first output terminal; and an amplifier circuit coupled to the first output terminal and the second output terminal, the amplifier circuit to output a voltage related to an environmental characteristic sensed by a sensing impedance element coupled to the coupling network.

Further embodiments of the present disclosure provide a sensor system that includes a driver circuit to generate a periodic stimulus signal; an impedance bridge including a first impedance element, a second impedance element, and a third impedance element, where the first impedance element is a variable impedance element; an input terminal coupled to the driver circuit and coupled to the impedance bridge to apply the stimulus signal to the impedance bridge; a coupling network coupled to a first output terminal of the impedance bridge; and an amplifier circuit coupled to the first output terminal and a second output terminal of the impedance bridge, the amplifier circuit configured to output a voltage based on signals from the first output terminal and the second output terminal.

Additional embodiments of the present disclosure provide a method for detecting a change in an environment characteristic, the method including determining, based on an offset impedance, a first impedance for a first impedance element arranged with a second impedance element and third impedance element as an impedance bridge; configuring the first impedance element according to the determined first impedance; applying a periodic stimulus signal to the impedance bridge; and receiving an output of the impedance bridge via a first output terminal and a second output terminal.

Still other embodiments of the present disclosure provide a sensor system that includes an impedance bridge including a first impedance element, a second impedance element, a third impedance element, and a coupling network arranged in a bridge configuration; a first input terminal coupled to the first impedance element and the second impedance element and configured to apply a first stimulus signal to the impedance bridge; a second input terminal coupled, in a first mode, to the coupling network and the third impedance element to apply a second stimulus signal to the impedance bridge; and at least one switch coupled to the second input terminal, the at least one switch controllable to decouple the second stimulus signal from the coupling network and the third impedance element in a second mode.

Further embodiments of the present disclosure provide a method for sensing impedance that includes receiving a first instruction to configure a sensor in a first mode, the sensor system including a first impedance element, a second impedance element, a third impedance element, and a coupling network arranged in a bridge configuration; in response to the first instruction, coupling the coupling network to a first electrode and a second electrode; receiving a second instruction to configure the sensor in a second mode; and in response to the second instruction, decoupling the coupling network from the second electrode.

Additional embodiments of the present disclosure provide a sensor system that includes an impedance bridge including a first impedance element, a second impedance element, a third impedance element, and a coupling network arranged in a bridge configuration; a driver circuit to generate, in a first mode, a first stimulus signal applied to a first input terminal of the impedance bridge, and to generate, in a second mode, a second stimulus signal and a third stimulus signal having an opposite phase of the second stimulus signal, the second stimulus signal applied to the first input terminal; and at least one switch coupled between the driver circuit and the impedance bridge, the at least one switch controllable to couple the third stimulus signal to the impedance bridge in the second mode.

As will be appreciated by one skilled in the art, aspects of the present disclosure, in particular aspects of a bridge-based impedance sensor and applications of the bridge-based impedance sensor, described herein, may be embodied in various manners (e.g., as a method, a system, a computer program product, or a computer-readable storage medium). Accordingly, aspects of the present disclosure may take the form of a hardware embodiment, a software embodiment (including firmware, resident software, micro-code, etc.), or an embodiment combining software and hardware aspects that may all generally be referred to herein as a "circuit," "module" or "system." Functions described in this disclosure may be implemented as an algorithm executed by one or more hardware processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer-readable medium(s), preferably non-transitory, having computer-readable program code embodied, e.g., stored, thereon. In various embodiments, such a computer program may, for example, be downloaded (updated) to the existing devices and systems (e.g. to the existing perception system devices and/or their controllers, etc.) or be stored upon manufacturing of these devices and systems.

The following detailed description presents various descriptions of specific certain embodiments. However, the innovations described herein can be embodied in a multitude of different ways, for example, as defined and covered by the claims and/or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Other features and advantages of the disclosure will be apparent from the following description and the claims.

Example Sensor System

FIG. 1 is a block diagram of a sensor system 100, according to some embodiments of the present disclosure. The impedance bridges and sensors described with respect to FIGS. 2-18 may be implemented in a system such as the sensor system 100.

The sensor system 100 includes a driver circuit 110, an impedance bridge 120, an amplifier circuit 130, a signal processing circuit 140, a sensor controller 150, an electrode switch 160, and electrodes 170. In alternative configurations, different, fewer, and/or additional components may be included in the sensor system 100 from those shown in FIG. 1. Furthermore, the functionality described in conjunction with one or more of the components shown in FIG. 1 may be distributed among the components in a different manner than described.

Figure 2:
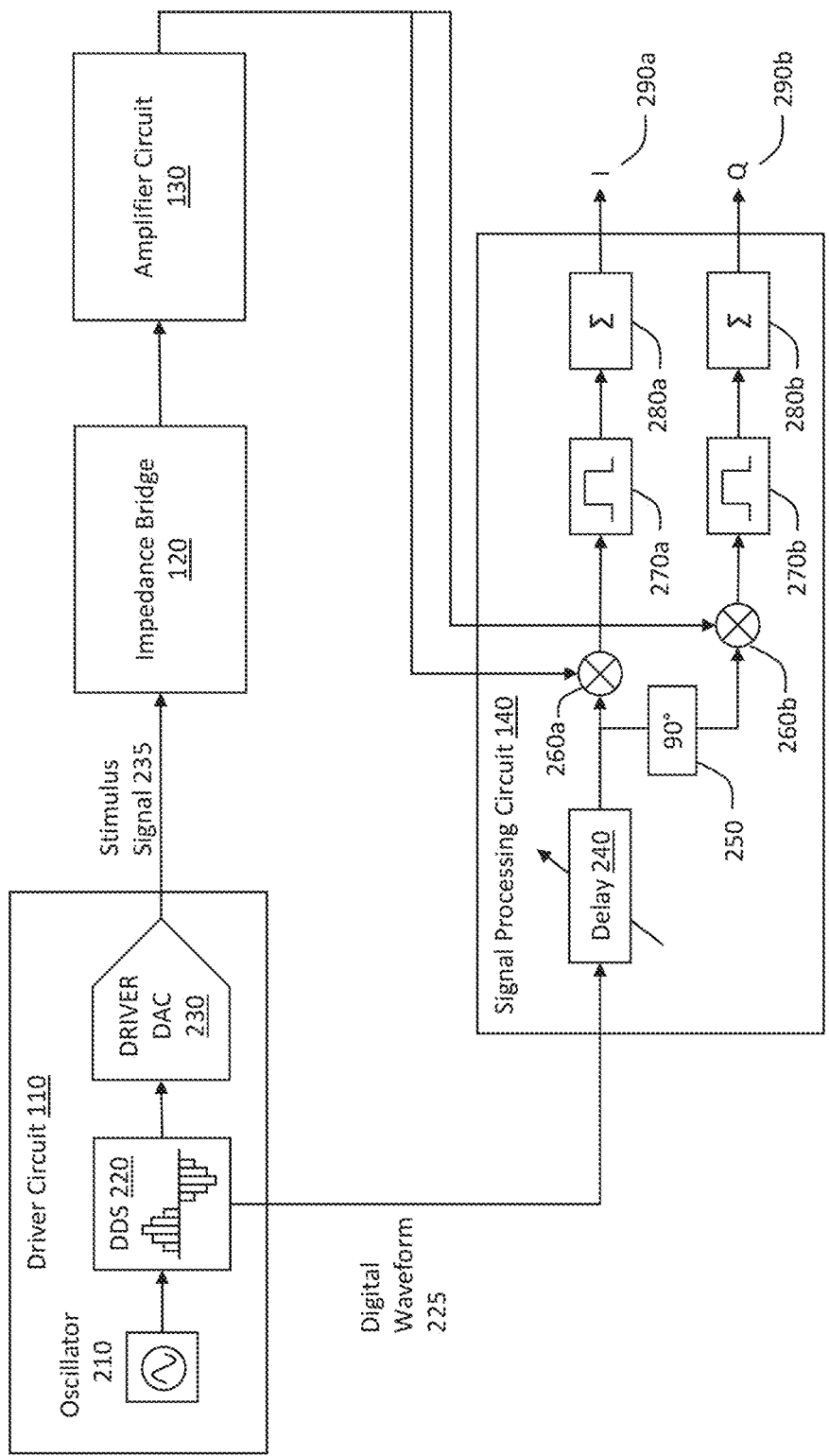
FIG. 2 is a block diagram showing the driver circuit and signal processing circuit of the sensor system in greater detail, according to some embodiments of the present disclosure.

The driver circuit 110 generates a stimulus signal that is applied to an input of the impedance bridge 120. The driver circuit 110 generates a periodic signal at a particular frequency, e.g., a sinusoidal signal, a square wave, a triangle wave, etc., and at a particular amplitude. The driver circuit 110 may be configured to adjust the frequency and/or amplitude of the stimulus signal. For example, the driver circuit 110 receives an instruction from the sensor controller 150 indicating the amplitude for the stimulus signal and the frequency for the stimulus signal, and the driver circuit 110 generates a stimulus signal having the instructed amplitude and frequency. The driver circuit 110 may generate a digital waveform that is converted to an analog signal used to drive the impedance bridge 120. The digital or analog waveform generated by the driver circuit 110 may also be provided to the signal processing circuit 140. An example implementation of the driver circuit 110 is shown in FIG. 2.

In some embodiments, the sensor controller 150 instructs the driver circuit 110 to generate a series of stimulus signals at different amplitudes and/or frequencies. In response, the driver circuit 110 generates a sequence of stimulus signals, e.g., a sequence of stimulus signals each having a different frequency. In some embodiments, the amplitude and/or frequency may be fixed. In some embodiments, the sensor controller 150 instructs the driver circuit 110 to generate a stimulus signal that includes multiple stimulus waves at multiple different frequencies, i.e., the stimulus waves at different frequencies are generated simultaneously rather than in a sequence. In response, the driver circuit 110 generates a multiplexed stimulus signal composed of multiple waves. This can reduce the time to perform a scan at multiple frequencies.

In some embodiments, the driver circuit 110 generates two stimulus signals with opposite phase. For example, to generate an antiphase signal, the driver circuit 110 passes a copy of the stimulus signal through an adjustable delay to delay the phase of the stimulus by signal 180°. The in-phase and antiphase signals are used in the mutual-sensing configuration described further below, in particular with respect to FIG. 5. A single stimulus signal may be used for the self-sensing configuration, as described with respect to FIG. 4.

The impedance bridge 120 receives the stimulus signal(s) from the driver circuit 110, and one or more of the electrodes 170 coupled to the impedance bridge 120 generate an electric field for sensing impedance in an environment around the impedance bridge 120. The impedance bridge 120 includes three impedance elements, a coupling network, and two output terminals. A first input terminal couples the driver circuit 110 to one side of the impedance bridge 120. A second input terminal couples another side of the impedance bridge 120 to the driver circuit 110 in the mutual-sensing mode; in the self-sensing mode, this side of the impedance bridge 120 is grounded. At least one of the impedance elements is variable, and the sensor controller 150 can adjust the variable impedance element(s) to balance the offset capacitance. When the stimulus signal or signals are applied to the impedance bridge 120, an electric field is generated in an environment of a sensing electrode (in the self-sensing mode) or a pair of sensing electrodes (in the mutual-sensing mode) coupled to the coupling network. A first output terminal is coupled between the coupling network and one of the impedance elements, and a second output terminal is coupled between the other two impedance elements. The voltage or charge difference between the two output terminals indicates the impedance in the region of the electric field. The impedance bridge is shown in greater detail in FIGS. 3-6B.

The amplifier circuit 130 is connected to the two output terminals of the impedance bridge 120 and is configured to detect and amplify a voltage based on signals from the two output terminals. The amplifier circuit 130 may include one or more programmable gain amplifiers (PGAs) that have adjustable gains; the PGA settings may be received from the sensor controller 150. The amplifier circuit 130 may further convert the analog voltage signal to a digital output; in other embodiments, the amplifier circuit 130 outputs an analog signal. In some embodiments, the configuration of the amplifier circuit 130 may change based on whether the sensor system 100 is in a mutual-sensing mode or self-sensing mode. The different configurations of the amplifier circuit 130 are described with respect to FIGS. 4 and 5.

The signal processing circuit 140 is coupled to the amplifier circuit 130 and processes the output of the amplifier circuit 130. The signal processing circuit 140 may also be coupled to the driver circuit 110 to receive a copy of the stimulus signal. The signal processing circuit 140 correlates the stimulus signal from the driver circuit 110 and the output signal to isolate the contribution of the impedance response at the specific frequency of the stimulus signal. The signal processing circuit 140 may demodulate the signal into in-phase and quadrature components. If the stimulus signal includes multiple stimulus frequencies as described above, the signal processing circuit 140 also demodulates the output signal into components for each of the stimulus frequencies. The signal processing circuit 140 outputs the demodulated signal to the sensor controller 150 for further processing, e.g., for calculating a capacitance measurement or permittivity measurement based on the demodulated output. An example implementation of the signal processing circuit 140 is shown in FIG. 2.

The sensor controller 150 controls the other components of the sensor system 100. The sensor controller 150 may instruct the driver circuit 110 to generate a particular stimulus for the impedance bridge, e.g., a sine wave at a particular amplitude and particular frequency. If the sensor system 100 can alternately be configured in the self-sensing mode and the mutual-sensing mode, the sensor controller 150 instructs the components of the sensor system 100 based on the selected mode. In particular, the sensor controller 150 can select a configuration for the amplifier circuit 130, and can select whether the impedance bridge 120 receives one stimulus signal or two stimulus signals having opposite phase from the driver circuit 110. The sensor controller 150 may instruct the driver circuit 110 to generate a stimulus signal for a specific mode, e.g., a stimulus signal with one frequency setting and/or amplitude setting in the self-sensing mode, and a stimulus signal with a different frequency setting and/or amplitude setting in the mutual-sensing mode. The sensor controller 150 may comprise one or more microprocessors or other types of circuitry.

In some embodiments, the sensor system 100 includes an electrode switch 160 configured to couple the impedance bridge 120 to electrodes 170. The electrode switch 160 may be an example of a coupling network and integrated into the impedance bridge 120, or the electrode switch may be connected to a coupling network included in the impedance bridge 120. For example, a device implementing the sensor system 100 includes a set of two or more sensing electrodes. In the self-sensing mode, the sensor controller 150 instructs the electrode switch 160 to select one of the sensing electrodes. In the mutual-sensing mode, the sensor controller 150 instructs the electrode switch 160 to select two of the sensing electrodes. The device electrodes 170 may also include a ground electrode, and the sensor system 100 may include a connection to the ground electrode to ground various elements of the circuitry within the sensor system 100.

Figure 7:
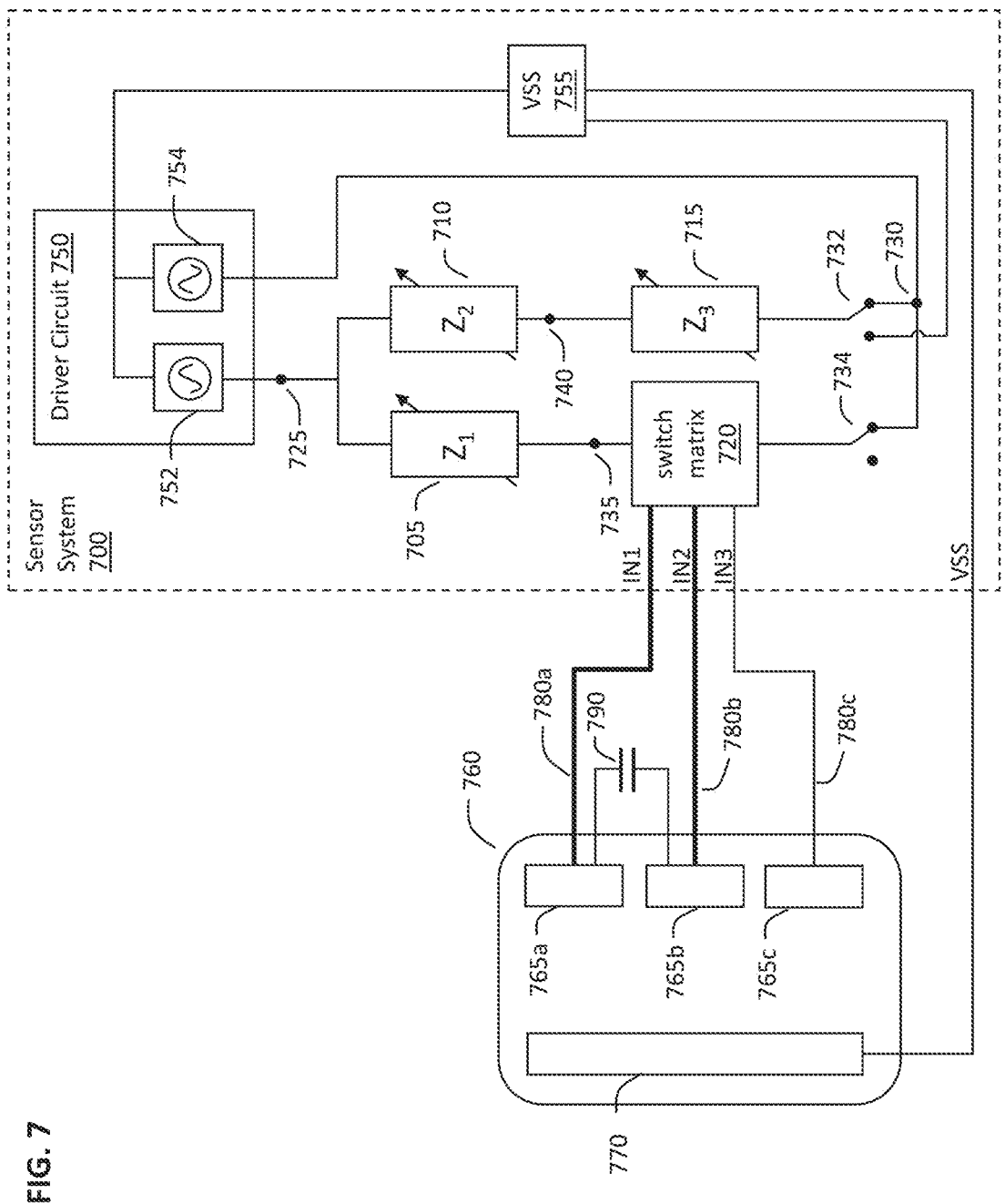
FIG. 7 is a block diagram of an example implementation of a sensor system implemented in a device and configured in a mutual-sensing mode, according to some embodiments of the present disclosure.
Figure 8:
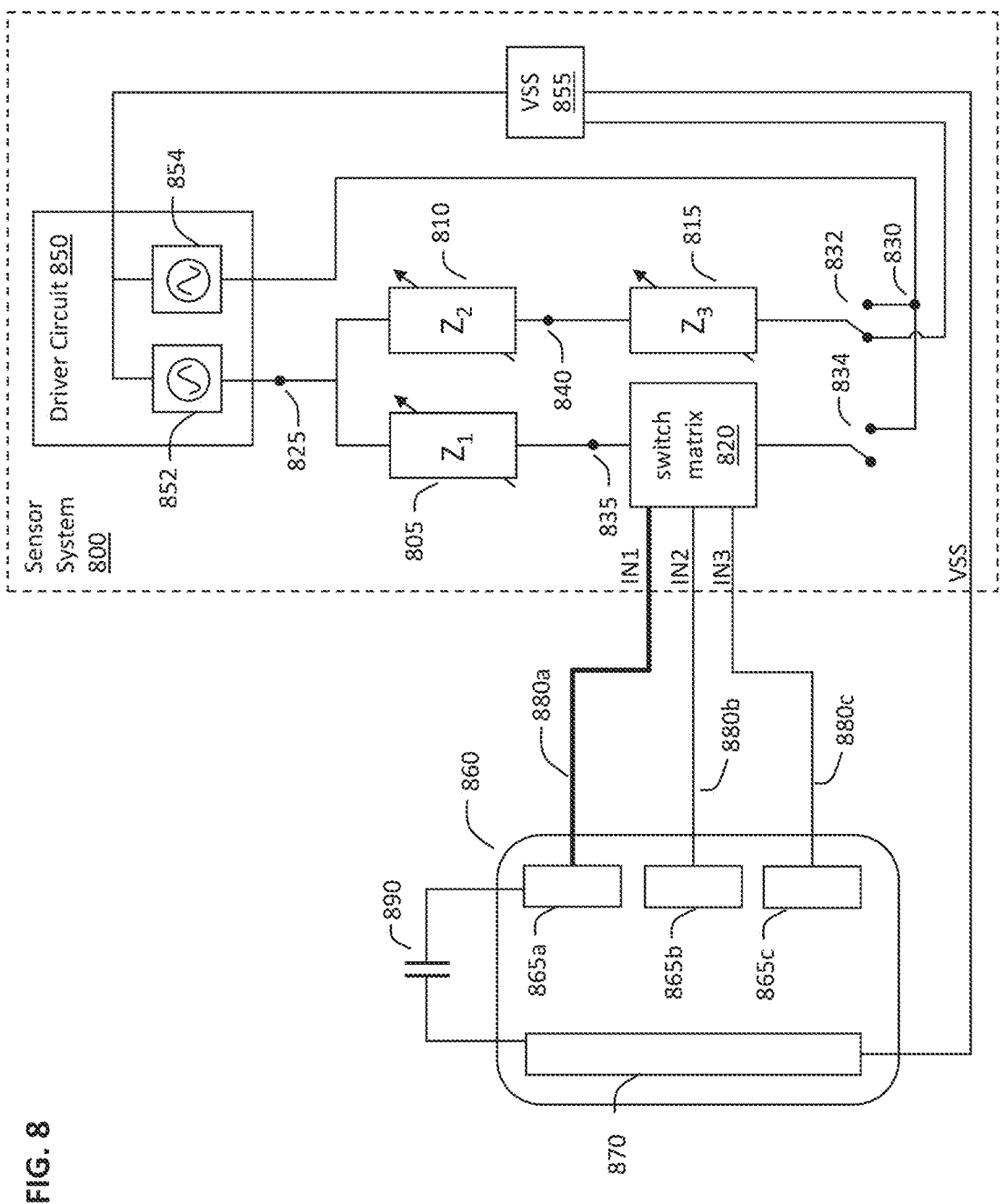
FIG. 8 is a block diagram of an example implementation of a sensor system implemented in a device and configured in a self-sensing mode, according to some embodiments of the present disclosure.

In one example, a first sensing electrode is fixedly coupled to one terminal of the coupling network, and a switch (e.g., the electrode switch 160) alternately connects another terminal of the coupling network to a second sensing electrode in the mutual-sensing mode. In another example, the electrode switch 160 may be a switch matrix that can couple the impedance bridge 120 to a different electrode selected from a set of electrodes that includes two or more sensing electrodes. In this example, the sensor controller 150 may select two of the electrodes 170 to observe an environment around a particular region of the device, and instruct the electrode switch 160 according to the selection. Examples of the switch matrix and electrodes 170 are shown in FIGS. 7 and 8, and the switch matrix and electrodes are described further with respect to these figures.

Example Driver Circuit and Signal Processing Circuit

FIG. 2 is a block diagram showing the driver circuit 110 and signal processing circuit 140 of the sensor system 100 in greater detail, according to some embodiments of the present disclosure. The driver circuit 110 includes an oscillator 210, a direct digital synthesizer (DDS) 220, and a driver digital-to-analog converter (DAC) 230. The oscillator 210 generates an oscillating signal with a fixed frequency that is used as a reference frequency. The oscillator 210 may be, for example, a crystal oscillator or a surface acoustic wave (SAW) oscillator.

The DDS 220 receives an input frequency from the sensor controller 150, as described above, and generates a digital waveform having the specified frequency. In the example shown in FIG. 2, the DDS 220 generates a digital sine wave. In other embodiments, the DDS 220 may be configured to generate a different waveform, or the DDS 220 may be configured to generate one of a plurality of waveforms selected by the sensor controller 150. The DAC 230 converts the digital output of the DDS 220 to the stimulus signal 235. The stimulus signal 235 is an analog waveform input to the impedance bridge 120.

The driver circuit 110 may include additional components to generate an antiphase signal (i.e., a signal having opposite phase of the stimulus signal 235) that is provided as a second input to the impedance bridge 120 in mutual-sensing mode. For example, the driver circuit 110 may include a delay element configured to receive either the digital waveform output by the DDS 220 or the analog waveform output by the DAC 230 and delay the received signal by 180°, generating an antiphase signal. The driver circuit 110 may have different configurations from the configuration shown in FIG. 2. For example, the driver circuit 110 may generate an analog waveform directly using a phase-locked loop (PLL).

The digital waveform 225 output by the DDS 220 and passed to the driver DAC 230 is also provided to the signal processing circuit 140. The signal processing circuit 140 performs a correlation of a digital output received from the amplifier circuit 130 with the digital waveform 225. The correlation process also demodulates the output from the amplifier circuit 130 into in-phase (I) and quadrature (Q) components 290. While in the example shown in FIG. 2 the correlation/demodulation process is performed in the digital domain, in other embodiments, the signal processing circuit 140 may receive the analog stimulus signal 235 from the driver circuit 110 and perform the correlation and demodulation in the analog domain.

More specifically, in the example shown in FIG. 2, the signal processing circuit 140 includes a delay element 240, a phase shifter 250, mixers 260, time domain windows 270, and accumulators 280. The delay element 240 delays the digital waveform 225 received from the DDS 220 to align the phase of the digital waveform 225 with the phase of the output of the amplifier circuit 130. The delay element 240 may be adjustable and calibrated for the device. In some embodiments, the delay setting of the delay element 240 may be adjusted based on the configuration of the impedance bridge 120 and/or amplifier circuit 130, as reconfiguring the impedance bridge 120 and amplifier circuit 130 may adjust the phase of the signal received from the amplifier circuit 130.

One copy of the digital waveform 225 delayed by the delay element 240 is passed to a first mixer 260a. Another copy of the delayed waveform is passed to a phase shifter 250 that shifts the phase of the delayed waveform by 90°. The 90° phase shift is used to obtain a quadrature component of the output signal.

The mixers 260a and 260b multiply their respective versions of the delayed digital waveform 225 with the output of the amplifier circuit 130. Delaying the digital waveform 225 and mixing the delayed waveform with the output of the amplifier circuit 130 correlates the output waveform to the input waveform. This has the effect of rejecting signals at frequencies other than the frequency of the digital waveform 225 and stimulus signal 235. For example, if the sensor system 100 is incorporated into a smartphone, the frequency of the electronics running the screen may interfere with the sensor system 100. The frequency of the waveform generated by the driver circuit 110 can be selected to be a different frequency from other device frequencies, such that the correlation process rejects signals at other frequencies in the output of the amplifier circuit 130.

The outputs of the mixers 260a and 260b are each passed through a respective one of the time domain windows 270a and 270b. The outputs of the time domain windows 270a and 270b are each coupled to a respective accumulator 280a and 280b, which generate the demodulated output, i.e., an I component 290a and a Q component 290b. The time domain windowing and accumulation sample the data for storage in memory and further processing by the sensor controller 150. The output signals 290a and 290b (referred to generally as the signal processing output 290) are passed to the sensor controller 150 for processing.

Example Impedance Bridge

Figures 3, 4:
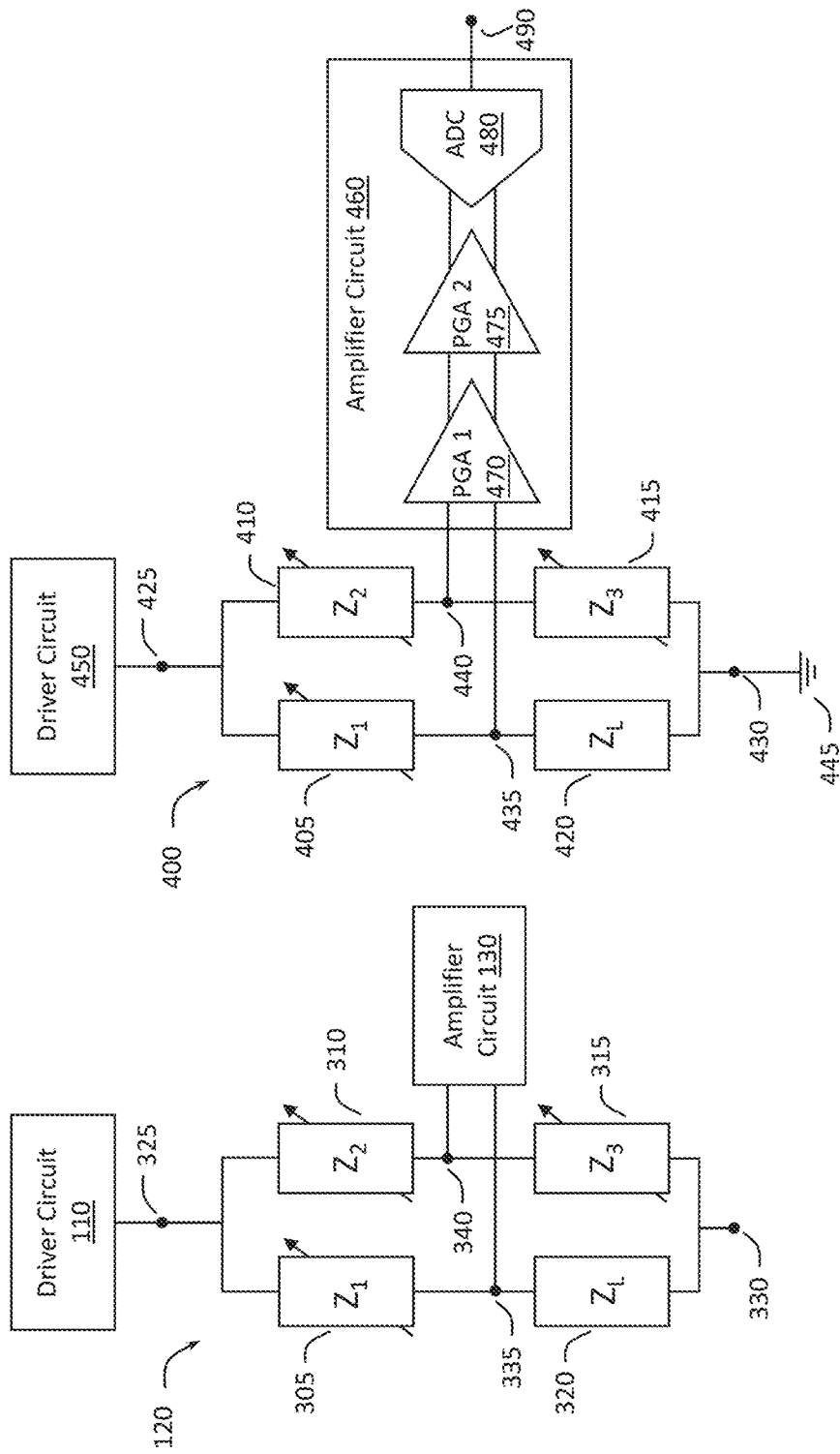
FIG. 3 is a block diagram of an example impedance bridge, according to some embodiments of the present disclosure.
FIG. 4 is a block diagram of an impedance bridge and amplifier circuit configured in a self-sensing mode, according to some embodiments of the present disclosure.

FIG. 3 is a block diagram of an example impedance bridge 120, according to some embodiments of the present disclosure. The impedance bridge 120 includes a first impedance element 305, a second impedance element 310, a third impedance element 315, and a coupling network 320. In this example, each of the first, second, and third impedance elements 305, 310, and 315 is a variable impedance element. Each impedance element 305, 310, and 315 may include one or more capacitors and/or one or more resistors. For example, each impedance element 305, 310, and 315 may include a variable capacitor and a variable resistor connected in series. Two example circuit implementations for the impedance elements 305, 310, and 315 are shown in FIGS. 6A and 6B.

Each of the first, second, and third impedance elements 305, 310, and 315 has a respective impedance $Z_1$, $Z_2$, and $Z_3$ that can be adjusted, e.g., by the sensor controller 150. For example, each impedance element 305, 310, and 315 includes a capacitor digital-to-analog converter (DAC), a programmable capacitor, or an adjustable capacitor having a set of possible capacitance settings, and a resistor DAC, a programmable resistor, or an adjustable resistor having a set of possible resistance settings. In some embodiments, one or more components of an impedance element may be bypassed, e.g., a resistor included in series with a capacitor may optionally be bypassed. In some embodiments, one or more of the impedance elements 305, 310, and 315 is fixed rather than variable. For example, for an impedance bridge 120 configured for the self-sensing mode, the third impedance element 315 may be fixed, and the first and second impedance elements 305 and 310 are variable. Furthermore, for an impedance bridge 120 configured for the mutual-sensing mode, both the second and third impedance elements 310 and 315 may be fixed, and the first impedance element 305 is variable. Having all three of the impedance elements 305, 310, and 315 be variable elements increases sensor size and complexity, but may also provide wider applicability, e.g., the ability to balance a wider range of offset impedances.

The coupling network 320 is a circuitry network within the impedance bridge 120 that is couplable to electrodes. In particular, the coupling network 320 couples the impedance bridge 120 to one sensing electrode to implement a self-sensing mode, and the coupling network 320 couples the impedance bridge 120 to two sensing electrodes to implement a mutual-sensing mode. The electrodes coupled to the coupling network 320 are referred to generally as a sensing impedance element. In some embodiments, the coupling network 320 includes one or more switches, e.g., a switching matrix, to switch between a set of sensing electrodes. The switching matrix may also ground electrodes that are not used for sensing. An example of a switching matrix is shown in FIGS. 7 and 8. The electrodes coupled to the coupling network 320 may be located outside of the impedance bridge 120 and, in some embodiments, outside of the sensor system 100. In other words, the coupling network 320 provides an electrical interface to couple the impedance bridge 120 to electrodes included in a device in which the sensor system 100 is integrated.

Figure 5:
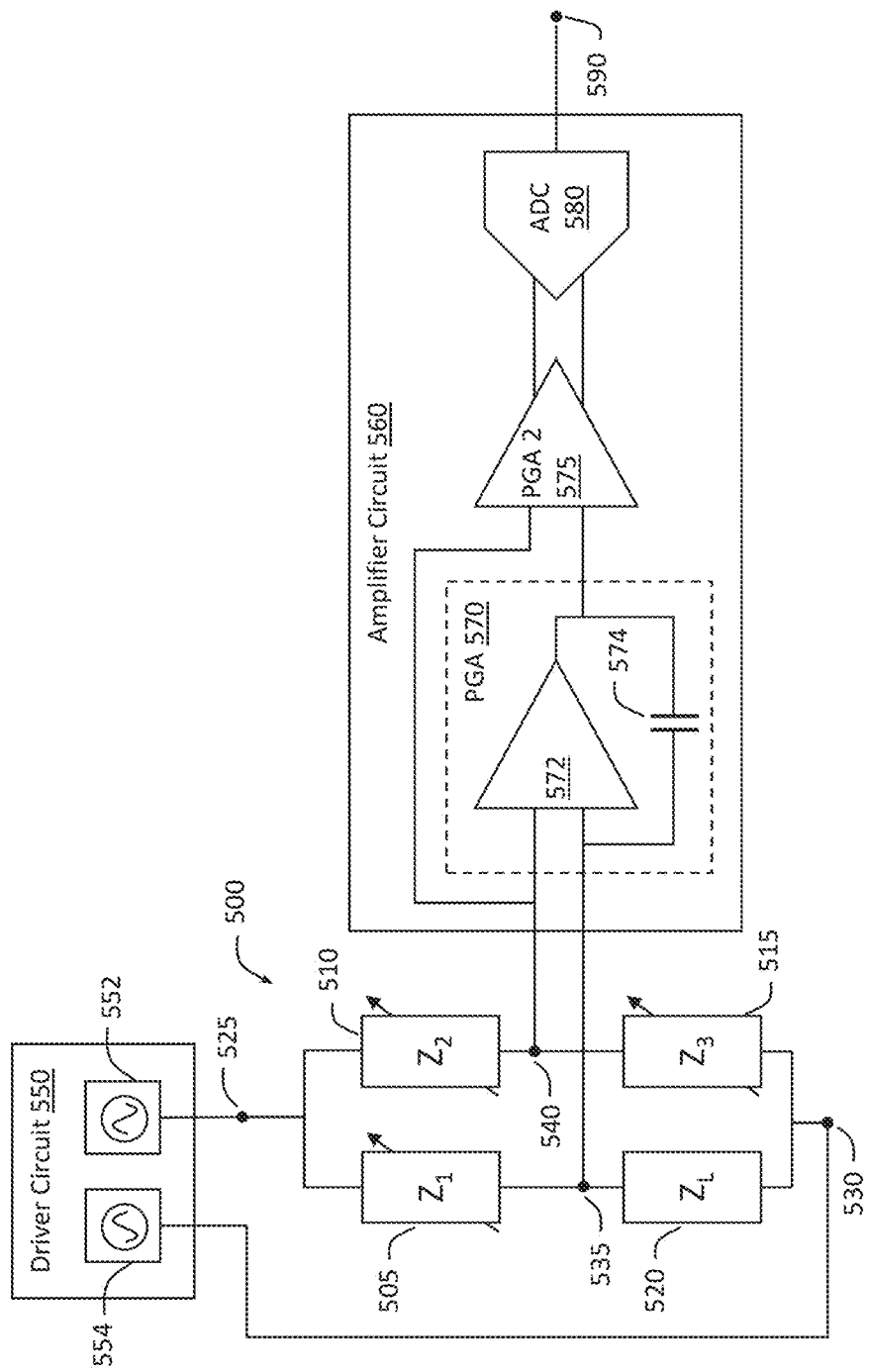
FIG. 5 is a block diagram of an impedance bridge and amplifier circuit arranged in a mutual-sensing mode, according to some embodiments of the present disclosure.
Figure 6:
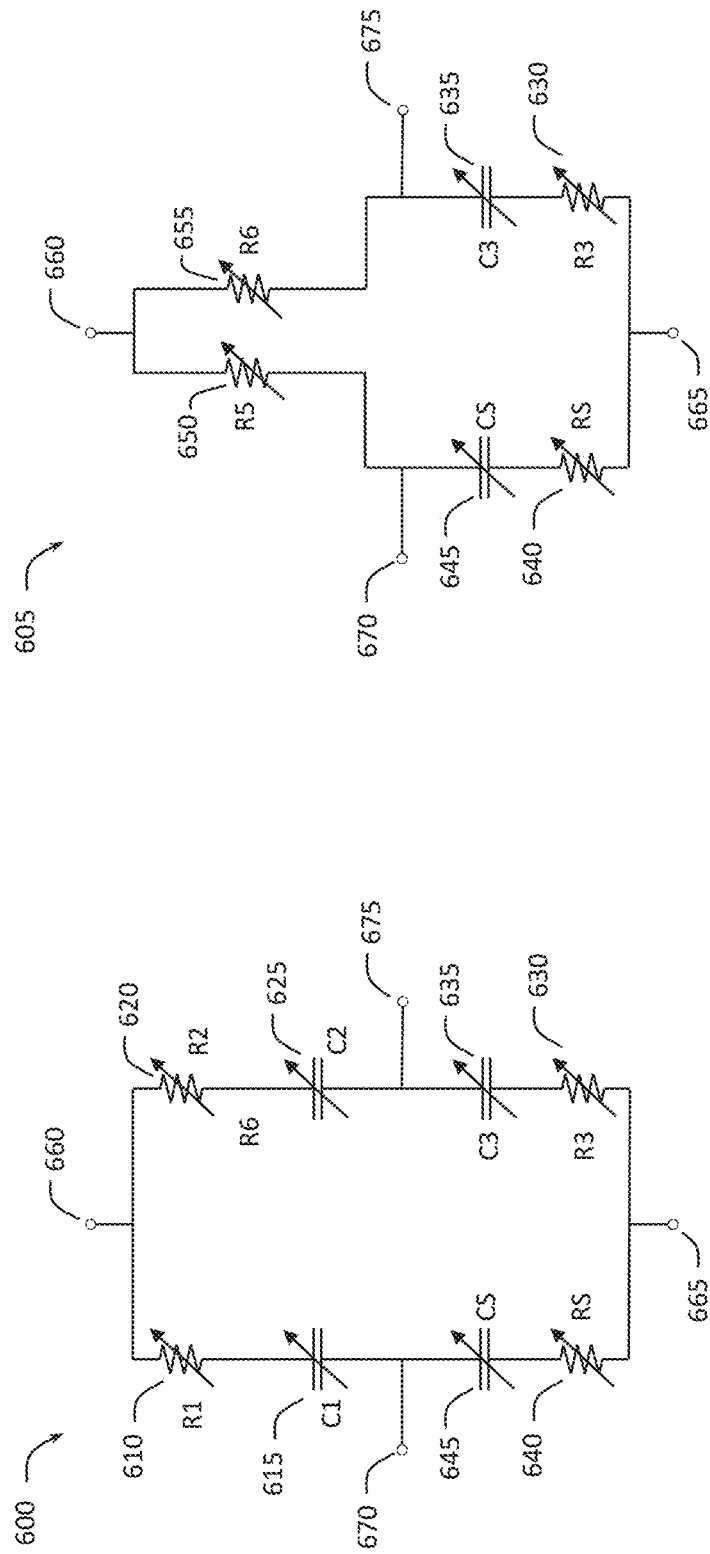
FIGS. 6A and 6B are circuit diagrams of an example impedance bridge, according to some embodiments of the present disclosure.

An input terminal 325, also referred to as a first input terminal 325, is coupled to the first impedance element 305 and the second impedance element 310. The first input terminal 325 is also coupled to the driver circuit 110 to apply the stimulus signal to the impedance bridge 120, and in particular, to apply the stimulus signal to the first impedance element 305 and the second impedance element 310. A second input terminal 330 is coupled to the third impedance element 315 and the coupling network 320. The second input terminal 330 is further coupled to either a ground, as shown in FIG. 4, or to the driver circuit 110, as shown in FIG. 5. In some embodiments, the second input terminal 330 includes or can be coupled to a switch or set of switches for switching the second input terminal 330 to the driver circuit 110 in the mutual-sensing mode. The switch is controllable to switch the second input terminal 330 between the ground in the self-sensing mode and the driver circuit 110 in the mutual-sensing mode. An example of two switches coupled to the second input terminal 330 for switching between the mutual-sensing and self-sensing modes is shown in FIGS. 7 and 8.

Two output terminals 335 and 340 couple the impedance bridge 120 to the amplifier circuit 130, which outputs a voltage related to an environmental characteristic sensed by the sensing impedance element. The first impedance element 305 is coupled between the input terminal 325 and a first output terminal 335. The second impedance element 310 is coupled between the input terminal 325 and a second output terminal 340. The third impedance element 315 is coupled between the second input terminal 330 and the second output terminal 340. The coupling network 320 is coupled between the second input terminal 330 and the first output terminal 335. In the self-sensing mode, the amplifier circuit 130 detects and amplifies a voltage difference between the first output terminal 335 and the second output terminal 340; this voltage difference is related to an environmental characteristic sensed by a sensing impedance element coupled to the coupling network 320. In the mutual-sensing mode, the amplifier circuit 130 converts a net charge at the first output terminal 335 to a voltage, and compares this voltage to a voltage at the second output terminal 340; this voltage difference indicates an imbalance in the bridge 120 caused by an environmental characteristic.

In operation, the environment around the sensing impedance element has an offset impedance load, referred to as $Z_L$. The offset impedance load may include a resistance component $R_L$ and a capacitance component $C_L$. The offset impedance load may be caused by other elements of the device implementing the sensor system 100, such as metallic or di-electric materials in the region of the sensing impedance element. In some embodiments, the offset impedance load $Z_L$ may be different for different configurations, e.g., whether the sensor system 100 is in self-sensing or mutual-sensing mode, or based on which electrodes are selected by the electrode switch 160. In some embodiments, the offset impedance load $Z_L$ for a particular device, or for a particular sensor configuration, is considered fixed. In other embodiments, the offset impedance load $Z_L$ may vary, e.g., based on device usage (e.g., whether certain components of the device are operating), environmental conditions (e.g., temperature, humidity), other device characteristics (e.g., whether the device is enclosed in a case), or other factors.

The impedance bridge 120 is balanced such that the offset impedance load $Z_L$ is offset by the impedances $Z_1$, $Z_2$, and $Z_3$ of the impedance elements 305, 310, and 315. In particular, setting a first ratio between the first impedance $Z_1$ and the offset impedance $Z_L$ equal to a second ratio between the second $Z_2$ and the third impedance $Z_3$ balances the impedance bridge 120. The sensor controller 150 may instruct the impedance bridge 120 to perform a calibration procedure to measure the offset impedance load (e.g., $R_S$ and $C_S$), and the sensor controller 150 sets one or more of the impedances $Z_1$, $Z_2$, and $Z_3$ according to the measured offset impedance load. The sensor controller 150 provides instructions to one or more of the impedance elements 305, 310, and 315, and in particular, to their constituent elements (e.g., variable capacitors and variable resistors) to adjust the impedances (e.g., some or all of $R_1$, $R_2$, and $R_3$; some or all of $C_1$, $C_2$, and $C_3$) to balance the offset impedance load $Z_L$.

More particularly, to balance the impedance bridge 120, the sensor controller 150 may determine the offset impedance $Z_L$ based on measurements obtained by the impedance bridge 120 or another sensor. The sensor controller 150 determines the first impedance $Z_1$ for the first impedance element 305 based on the offset impedance $Z_L$ and provides instructions to the first impedance element 305 to set it to the determined first impedance setting. For example, the sensor controller 150 adjusts the first impedance $Z_1$ to match or approximately match the offset impedance $Z_L$. The first impedance element $Z_1$ may have a finite number of impedance settings, and the sensor controller 150 selects the impedance setting that most closely matches the offset impedance $Z_L$. In another example, if the offset impedance $Z_L$ (e.g., the inverse of the offset capacitance $C_L$) is lower than the first impedance element 305 may be set to (e.g., the offset capacitance $C_L$ is higher than the highest capacitance setting in a programmable capacitor), the selected first impedance $Z_1$ is different from the offset impedance $Z_L$.

In some embodiments, only the first impedance $Z_1$ is variable, and the sensor controller 150 instructs the first impedance element 305 according to the selected first impedance $Z_1$ to balance the impedance bridge 120. In other embodiments, the second and/or third impedances $Z_2$ and $Z_3$ are also variable. In such embodiments, the sensor controller 150 selects the second and/or third impedances $Z_2$ and $Z_3$ based on the offset impedance $Z_L$ and the selected first impedance $Z_1$. The sensor controller 150 selects the second and/or third impedances $Z_2$ and $Z_3$ such that the first ratio $Z_1/Z_L$ is equal to the second ratio $Z_2/Z_3$. In one example, the first, second, and third impedances $Z_1$, $Z_2$, and $Z_3$ are all set equal or approximately equal to $Z_L$. In another example, the first impedance $Z_1$ is set equal or approximately equal to $Z_L$, and the second and third impedances $Z_2$ and $Z_3$ are equal to each other but not equal to $Z_L$, e.g., $Z_2$ and $Z_3$ are less than $Z_1$. In still another example, the first impedance $Z_1$ is less than $Z_L$, and the second impedance $Z_2$ is less than the third impedance $Z_3$. The second impedance $Z_2$ may also be less than the first impedance $Z_1$, and the third impedance $Z_3$ less than the offset impedance $Z_L$, to balance an offset load that is greater than highest impedance setting of the impedance elements 305, 310, and 315.

Example Impedance Bridge Configured for Self-Sensing Mode

FIG. 4 is a block diagram of an impedance bridge 400 and amplifier circuit 460 configured in a self-sensing mode, according to some embodiments of the present disclosure. The impedance bridge 400 is an example of the impedance bridge 120 described with respect to FIGS. 1-3. A first input terminal 425 couples the impedance bridge 120 (particularly, the first impedance element 405 and the second impedance element 410) to a driver circuit 450, which is an example of the driver circuit 110 described with respect to FIGS. 1 and 2. A first output terminal 435 is coupled between the first impedance element 405 and a coupling network 420, and a second output terminal 440 is coupled between the second impedance element 410 and the third impedance element 415. The first output terminal 435 and second output terminal 440 are further coupled to an amplifier circuit 460, which is an example of the amplifier circuit 130. A second input terminal 430 is coupled to a ground 445. The third impedance element 415 is coupled between the second output terminal 440 and the ground 445, and the coupling network 420 is coupled between the first output terminal 435 and the ground 445. More particularly, a switch coupled to a terminal of the third impedance element 415 may be coupled to a ground, while the capacitive path of the sensing impedance element coupled to the coupling network 420 spans from a sensing electrode coupled to the coupling network 420 and a ground 445. This arrangement is shown in FIG. 8.

The amplifier circuit 460 includes one or more differential amplifiers for amplifying a difference between the first and second output terminals 435 and 440. In the example shown in FIG. 4, the amplifier circuit 460 includes a cascade of a first programmable gain amplifier (PGA) 470 and a second PGA 475. Each PGA 470 and 475 may have an adjustable gain. The sensor controller 150 may select a gain setting and instruct the amplifier circuit 460 to adjust the gains of the PGAs 470 and 475 accordingly. The number of PGAs and gain settings for each PGA included in the amplifier circuit determines the total gain available to the amplifier circuit 460. The first and second PGAs 470 and 475 are fully differential amplifiers that receive two inputs and provide two outputs. The two outputs of the first PGA 470 are coupled to the two inputs of the second PGA 475. The two outputs of the second PGA 475 are coupled to inputs of an analog-to-digital converter (ADC) 480. The ADC 480 converts the amplified difference signal to a digital output 490. The digital output 490 is coupled to a signal processing circuit, e.g., the signal processing circuit 140 shown in FIGS. 1 and 2. In other embodiments, the ADC 480 is omitted, and the amplifier circuit 460 provides an analog output signal to the signal processing circuit 140.

Example Impedance Bridge Configured for Mutual-Sensing Mode

FIG. 5 is a block diagram of an impedance bridge 500, driver circuit 550, and amplifier circuit 560 configured in a mutual-sensing mode, according to some embodiments of the present disclosure. The impedance bridge 500 is an example of the impedance bridge 120 described with respect to FIGS. 1-3. A first input terminal 525 couples the impedance bridge 120 (particularly, the first impedance element 505 and the second impedance element 510) to a driver circuit 550, which is an example of the driver circuit 110 described with respect to FIGS. 1 and 2. The driver circuit 550 generates two signals, a first signal 552 and a second signal 554 that has an opposite phase of the first signal 552. The first signal 552 and second signal 554 are also referred to as phase and antiphase signals. The first signal 552 is provided to the input terminal 525. The second signal 554 is provided to a second input terminal 530, which is coupled to a coupling network 520 and a third impedance element 515.

The coupling network 520 is coupled to two or more sensing electrodes, as described with respect to FIG. 7.

A first output terminal 535 is coupled between the first impedance element 505 and the coupling network 520, and a second output terminal 540 is coupled between the second impedance element 510 and the third impedance element 515. The first output terminal 535 and second output terminal 540 are further coupled to an amplifier circuit 560, which is an example of the amplifier circuit 130. The third impedance element 515 is coupled between the second output terminal 540 and the second input terminal 530, and the coupling network 520 is coupled between the first output terminal 535 and the second input terminal 530. When the impedance bridge 500 is balanced, the opposing stimulus signals 552 and 554 cancel out at the output terminals 535 and 540. A DC offset voltage may be applied to output terminals 535 and 540 to set these to fixed voltage. A change in the environment around the electrodes coupled to the coupling network 520 changes the charge level at the output terminal 535.

The amplifier circuit 560 includes two PGAs 570 and 575. Each PGA 570 and 575 may have an adjustable gain, and the sensor controller 150 selects a gain setting and instructs the amplifier circuit 560 to adjust the gains of the PGAs 570 and 575 accordingly. The first PGA 570 includes an amplifier 572 and a feedback capacitor 574 coupled to the output of the amplifier 572. The feedback capacitor 574 is also connected to the input of the amplifier 572 that is connected to the first output terminal 535. The first PGA 570 converts a net charge due to an imbalance in the impedance bridge 500 to an output voltage. The feedback capacitor 574 may be a variable capacitor, and its capacitance can be set by the sensor controller 150 based on the capacitance response across the electrodes coupled to the coupling network 520. Reducing the capacitance of the feedback capacitor 574 reduces the noise in the measured impedance but also reduces the range of impedance loads the sensor system can measure, while a higher capacitance setting for the feedback capacitor 574 increases the measurement range but also may increase the noise in the impedance measurement. If the capacitance response across the electrodes coupled to the coupling network 520 has a relatively large amount of variation, the feedback capacitor 574 may saturate, increasing the noise in the resulting output signal. Therefore, when variation in capacitance across the electrodes coupled to the coupling network 520 is greater, the sensor controller 150 may select greater capacitance setting for the feedback capacitor 574.

The second PGA 575 has a first input coupled to the second output terminal 540 and a second input that is coupled to the output of the first PGA 570. The second PGA 575 amplifies a difference between the voltage at the second output terminal 540 and the output voltage of the PGA 570. The two outputs of the second PGA 575 are coupled to inputs of an ADC 580. The ADC 580 converts the amplified difference signal to a digital output 590. The digital output 590 is coupled to a signal processing circuit, e.g., the signal processing circuit 140 shown in FIGS. 1 and 2. In other embodiments, the ADC 580 is omitted, and the amplifier circuit 560 provides an analog output signal to the signal processing circuit 140.

In some embodiments, the sensor systems shown in FIGS. 4 and 5 are two different configurations of the same sensor system, e.g., two different configurations of sensor system 100. The second input terminal 430 and 530 includes a switch or switches to either couple the impedance bridge to the driver circuit, as shown in FIG. 5, or to couple the impedance bridge to a ground, as shown in FIG. 4; example switches are shown in FIGS. 7 and 8. The amplifier circuit 130 has switchable connections between the PGAs that enable the first PGA to be connected to the impedance bridge 120 and to the second PGA either as shown in FIG. 4 or FIG. 5. The sensor controller 150 provides instructions to the switch(es) at the second input terminal and instructions to the amplifier circuit to configure the sensor system 100 in either of the modes shown in FIG. 4 or FIG. 5. In some other embodiments, the amplifier circuit 130 includes both of the amplifier circuits 460 and 560, and the sensor controller 150 selects one of the amplifier circuits 460 and 560 and couples the selected amplifier circuit to the impedance bridge 120 and signal processing circuit 140 based on the selected sensing mode.

Example Impedance Bridge Circuit Diagram

FIGS. 6A and 6B show two circuit diagrams of two circuit configurations 600 and 605 of an example impedance bridge, according to some embodiments of the present disclosure. The circuit diagrams shown in FIGS. 6A and 6B may be two configurations of the impedance bridges 120, 400, and 500 described with respect to FIGS. 1-5. In some embodiments, the impedance bridge 120 may alternate between the configurations shown in FIGS. 6A and 6B. The first configuration 600 is referred to as a capacitor bridge configuration, and the second configuration 605 is referred to as a resistor pullup configuration.

The first configuration 600 includes a first resistor 610 and a first capacitor 615 connected in series and coupled between a first input terminal 660 and a first output terminal 670. The first resistor 610 and first capacitor 615 are an example of the first impedance elements 305, 405, and 505 shown in FIGS. 3-5. The first configuration 600 includes a second resistor 620 and a second capacitor 625 connected in series and coupled between the first input terminal 660 and a second output terminal 675. The second resistor 620 and second capacitor 625 are an example of the second impedance elements 310, 410, and 510 shown in FIGS. 3-5. The first configuration 600 includes a third resistor 630 and a third capacitor 635 connected in series and coupled between a second input terminal 665 and the second output terminal 675. The third resistor 630 and third capacitor 635 are an example of the third impedance elements 315, 415, and 515 shown in FIGS. 3-5. In this example, each of the resistors 610, 620, and 630 is a variable resistor; their respective resistances R1, R2, and R3 may be set by the sensor controller 150.

Each of the capacitors 615, 625, and 635 is a variable capacitor; their respective capacitances C1, C2, and C3 may be set by the sensor controller 150. As noted above, in some implementations, one or more of the resistors 610, 620, and 630 and/or capacitors 615, 625, and 635 may be fixed.

The first configuration 600 further includes a sensed resistance 640 and a sensed capacitance 645. The sensed resistance 640 and sensed capacitance 645 are models of the resistance and capacitance across the electrodes coupled to the coupling network. The sensed resistance 640 and sensed capacitance 645 may have an offset component, i.e., the offset impedance load described with respect to FIGS. 1-5. The sensed resistance 640 and sensed capacitance 645 may also have a load that varies based on environmental conditions, such as a tissue sample, a finger, or another material in the environment of the electrode(s).

FIG. 6B shows a second configuration 605 of an example impedance bridge. In the second configuration 605, the first and second series resistors 610 and 620 and first and second series capacitors 615 and 625 have been replaced with two pullup resistors 650 and 655. The pullup resistors 650 and 655 enable measurement of a small change in capacitance when the offset capacitance is large.

The impedance bridge 120 may be able to alternate between the first configuration 600 and second configuration 605. In one embodiment, the first and fifth resistors 610 and 650 are the same, and the second and sixth resistors 620 and 655 are the same; the impedance bridge 120 switches from the first configuration 600 to the second configuration 605 by bypassing the capacitors 615 and 625. Alternatively, the impedance bridge may include one pair of pathways between the terminals 670 and 660 and another pair of pathways between the terminals 675 and 660, and switches to select one pathway of each of the pair of pathways. In some embodiments, the impedance bridge may be configured so that the circuit simultaneously includes both pathways between the terminals 670 and 660 and both pathways between the terminals 675 and 660, i.e., the pathways including the first and second resistors 610 and 620 and first and second capacitors 615 and 625, as well as the pathways including the fifth and sixth resistors 650 and 655, with the fifth and sixth resistors connected in parallel to the first and second resistors 610 and 620 and the first and second capacitors 615 and 625.

The resistor pullup configuration 605 shown in FIG. 6B is useful for measuring loads with large offset capacitance. When the available capacitance on the impedance bridge is less than the offset capacitance (e.g., the offset load has a greater capacitance than the largest available capacitance setting for $C_1$), the resistor pullup configuration 605 can be used to achieve a better signal-to-noise ratio than may be achieved with capacitor bridge 600 configuration, so the sensor controller 150 may select the resistor pullup configuration 605. On the other hand, when the offset capacitance is less than the available capacitance on the impedance bridge, the capacitor bridge configuration 600 may provide better signal-to-noise ratio than the resistor pullup configuration 605, so the sensor controller 150 may select the capacitor bridge configuration 600. While the impedance bridge may be designed with larger on-chip capacitances to improve signal-to-noise ratio for larger loads, this also increases the amount of the die dedicated to the on-chip capacitors, and may increase the size of the chip. Implementing a resistor pullup configuration 605 can be used to improve noise performance at high loads without constraining chip area or increasing chip size.

Example Device With Impedance Bridge Sensor

FIG. 7 is a block diagram of an example implementation of a sensor system 700 implemented in a device 760 and configured in a mutual-sensing mode, according to some embodiments of the present disclosure. The sensor system 700 is an example of the sensor system 100, and more particularly, an example of the mutual-mode sensor system shown in FIG. 5. The sensor system 700 includes an impedance bridge having three impedance elements 705, 710, and 715 and a switch matrix 720, which is an example implementation of a coupling network 320. A first input terminal 725 is coupled to a driver circuit 750, which is an example of the driver circuit 110. A second input terminal 730 is also coupled to the driver circuit 750. The second input terminal 730 is coupled to a first switch 732 configurable to couple the third impedance element 715 to the driver circuit 750. The second input terminal 730 is also coupled to a second switch 734 configurable to couple the switch matrix 720 to the driver circuit 750. In the mutual-sensing mode shown in FIG. 7, the switches 732 and 734 are configured to couple the third impedance element 715 and switch matrix 720, respectively, to the second input terminal 730 and thus to the driver circuit 750. In the self-sensing mode shown in FIG. 8, the switch 732 couples the third impedance element 715 to a ground element, VSS 755, and the switch 734 floats the lower terminal of the switch matrix 720.

The driver circuit 750 generates a first stimulus signal 752 and second stimulus signal 754 having opposite phase of the first stimulus signal 752. The first stimulus signal 752 is coupled to the first input terminal 725, and the second stimulus signal 754 is coupled to the second input terminal 730. The second stimulus signal 754 is applied to the switch matrix 720 and third impedance element 715 based on the configurations of the switches 734 and 732. The impedance bridge has two outputs 735 and 740, which are connected to an amplifier circuit (e.g., amplifier circuit 130 or 560) not shown in FIG. 7. In addition to the amplifier circuit, the sensor system 700 may further include a signal processing circuit (e.g., signal processing circuit 140) and control circuitry (e.g., sensor controller 150).

The switch matrix 720 is couplable to electrodes on the device 760. In this example, the device 760 includes three electrodes 765a, 765b, and 765c arranged along one side of the device 760; these may be sensing electrodes. The device 760 includes a fourth electrode 770 arranged along another side of the device 760; the fourth electrode 770 may be a ground electrode. The device 760 may include any number of sensing electrodes 765 and any number of ground electrodes 770. The sensor system 700 includes pins IN1, IN2, IN3, and VSS for coupling to the electrodes on the device 760. For example, the first electrode 765a is coupled to a first input pin IN1 on the sensor system 700 via connection 780a. The first input pin IN1 is coupled to an input of the switch matrix 720. The ground electrode 770 is connected via a VSS pin to a ground element VSS 755 on the sensor system 700. The VSS 755 acts as a ground for circuitry within the sensor system 700. Note that while FIG. 7 depicts the sensor system 700 as being outside of the device 760, it should be understood that the sensor system 700 may be integrated into the device 760 as a component or subsystem of the device 760.

The switch matrix 720 includes circuitry for coupling the first output terminal 735 and the second input terminal 730 to electrodes of the device 760. In the example shown in FIG. 7, the switch matrix 720 selects the first sensing electrode 765a and the second sensing electrode 765b, as indicated by the heavier connection lines 780a and 780b, e.g., the switch matrix 720 couples the first output terminal 735 to the first electrode 765a and the second input terminal 730 to the second electrode 765b, or vice versa. In some embodiments, the switch matrix 720 further couples any unused sensing electrodes (here, the third electrode 765c) to the VSS 755 to ground the unused sensing electrodes. The switch matrix 720 may alternately be set to couple the first output terminal 735 and second input terminal 730 to any pair of electrodes 765. The switch settings may be determined by the sensor controller 150, which transmits configuration instructions to the electrode switch matrix 720 and the switches 732 and 734. In this configuration, the output of the impedance bridge is correlated to a change in capacitance between the selected electrodes 765a and 765b. This is represented by the sensed capacitance 790 between the selected electrodes 765a and 765b. At least a portion of the electric field between the electrodes 765a and 765b extends outside of the device 760 and is able to sense changes in the environment outside of the device 760.

In some embodiments, the switch matrix 720 may couple the first output terminal 735 and/or second input terminal 730 to multiple electrodes 765. For example, if the device 760 includes a first pair of electrodes on one side of a device and a second pair of electrodes on another side of the device, the switch matrix 720 may couple the first pair of electrodes to the first output terminal 735 and the second pair of electrodes to the second input terminal 730. This may enable the sensor system 700 to obtain an impedance measurement across a larger region.

FIG. 8 is a block diagram of an example implementation of a sensor system 800 implemented in a device 860 and configured in a self-sensing mode, according to some embodiments of the present disclosure. The sensor system 800 may be the sensor system 700 reconfigured for self-sensing mode, and the device 860 may be the device 760. The sensor system 800 includes an impedance bridge having three impedance elements 805, 810, and 815 and a switch matrix 820. A first input terminal 825 is coupled to a driver circuit 850, and a second input terminal 830 is also coupled to the driver circuit 850. The second input terminal is coupled to a first switch 832 configurable to couple the third impedance element 815 to the driver circuit 850. The second input terminal 830 is also coupled to a second switch 834 configurable to couple the switch matrix 820 to the driver circuit 850. In the self-sensing mode shown in FIG. 8, the switch 832 is configured to couple the third impedance element 815 to a ground element, VSS 855, and the switch 834 is configured to float the lower terminal of the switch matrix 820.

The driver circuit 850 generates a first stimulus signal 852, and in the self-sensing mode, the driver circuit 850 may or may not generate the second stimulus signal 854. The first stimulus signal 852 is coupled to the first input terminal 825, but the second stimulus signal 754 is not coupled to the impedance bridge. The impedance bridge has two outputs 835 and 840, which are connected to an amplifier circuit (e.g., amplifier circuit 130 or 560) not shown in FIG. 8. In addition to the amplifier circuit, the sensor system 800 may further include a signal processing circuit (e.g., signal processing circuit 140) and control circuitry (e.g., sensor controller 150).

As noted with respect to FIG. 7, the switch matrix 820 is couplable to electrodes on the device 860, and in particular, to electrodes 865a, 865b, 865c. Electrodes 865a, 865b, 865c, and 870 are the same as the electrodes 765a, 765b, 765c, and 770 described with respect to FIG. 7, and are connected to the sensor system 800 and, in particular, to the switch matrix 820 and VSS 855, in the same manner. In the example shown in FIG. 8, the switch matrix 820 selects the first sensing electrode 865a, as indicated by the heavier connection line 880a. In particular, the switch matrix 820 couples the first output terminal 835 to the first electrode 865a. In some embodiments, the switch matrix 820 further couples the other sensing electrodes 865b and 865c to the VSS 855. The switch matrix 820 may alternately be set to couple the first output terminal 835 to any of the electrodes 865, or to multiple electrodes simultaneously (e.g., electrodes 865b and 865c) to obtain an impedance measurement across a wider area. The settings for the switch matrix 820 and the switches 832 and 834 may be determined by the sensor controller 150, which transmits configuration instructions to the electrode switch matrix 820 and switches 832 and 834. In this configuration, the output of the impedance bridge is correlated to a change in an electric field in an environment of the selected sensing electrode 865a, and in particular, in an electric field that extends from the selected sensing electrode 865a, through an environment around the device 860, and to the ground electrode 870. This is represented by the sensed capacitance 890 between the selected electrodes 865a and ground, represented by the ground electrode 870.

In some embodiments, the sensor controller 150 instructs the switches 820, 832, and 834 to cycle through a series of different configurations and obtain a sequence of measurements, e.g., measurements in different modes, and/or measurements from different electrodes or combinations of electrodes. As one example, the sensor controller 150 instructs the sensor system 100 to obtain sequence of self-mode measurements using each of the sensing electrodes 865 in series (e.g., a first measurement using the first sensing electrode 865a, a second measurement using the second sensing electrode 865b, etc.). As another example, the sensor controller instructs the sensor system 100 to obtain a sequence of mutual-mode measurements using different combinations of the sensing electrodes 865 (e.g., a first measurement between the electrodes 765a and 765b, a second measurement between the electrodes 765b and 765c, etc.). The sensor controller 150 may switch back and forth between self-sensing and mutual-sensing modes and obtain measurements in each mode. The sensor controller 150 may adjust one or more of the impedance settings Z1, Z2, and Z3 based on the selected electrode(s) and selected mode to account for different offset impedances. In some embodiments, the sensor controller 150 further instructs the driver circuit 110 to generate different signal frequencies and/or amplitudes for different measurements. For example, the sensor controller 150 instructs the electrode matrix 820 to select the first electrode 865a and obtains a series of measurements from the first electrode 865a at a set of different stimulus frequencies; the sensor controller 150 then instructs the electrode matrix 820 to select the second electrode 865b and obtains a series of measurements from the second electrode 865b at the set of stimulus frequencies, etc. Various combinations of sensing mode, electrode selection, frequency selection, and amplitude selection are possible.

Methods for Using Sensor System

Figure 9:
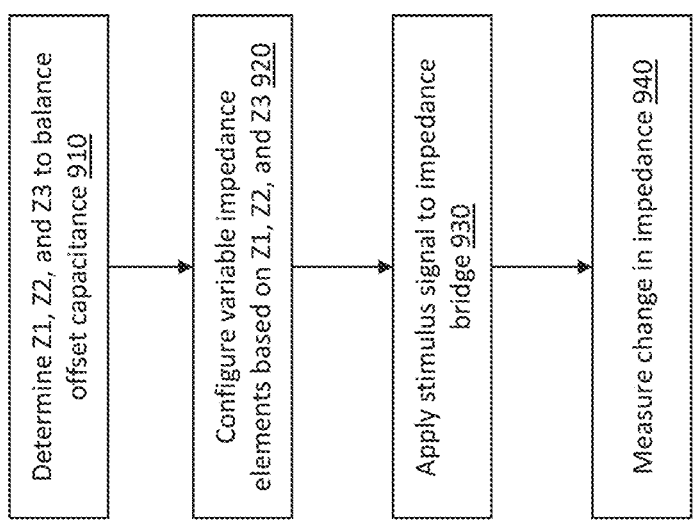
FIG. 9 provides a method for sensing a change in impedance using a sensor system, according to some embodiments of the present disclosure.

FIG. 9 provides a method for sensing a change in impedance using the sensor system, according to some embodiments of the present disclosure. Circuitry, e.g., the sensor controller 150, determines 910 impedance settings Z1, Z2, and Z3 for the impedance elements 305, 310, and 315 to balance an offset capacitance on the sensor, e.g., on a selected electrode or across a selected pair of electrodes. In some embodiments, one or more of the impedance elements are fixed, and the circuitry determines impedance settings for the variable elements, e.g., the circuitry determines a first impedance Z1 for the first impedance element 305 based on the offset impedance, the second impedance Z2, and the third impedance Z3.

The circuitry configures 920 the variable impedance elements based on the selected impedances. For example, the circuitry transmits instructions to adjust a variable capacitor included in the first impedance element 305 to set the capacitance to a determined capacitance.

A driver circuit, e.g., the driver circuit 110, applies 930 a stimulus signal to the impedance bridge. The driver circuit 110 may generate the stimulus signal at a particular frequency or amplitude at the instruction of the circuitry. In some embodiments, the driver circuit 110 generates and applies two stimulus signals having opposite phases to opposite sides of the impedance bridge, as described above.

The circuitry receives an output of the impedance bridge via a pair of output terminals and measures 940 a change in impedance caused by a change in an environment of the electrode or electrodes. For example, the amplifier circuit 130 and signal processing circuit 140 generate a demodulated and digitized output signal to the sensor controller 150, which can determine a change in impedance relative to the offset impedance based on the output signal. The sensor controller 150 may compare the impedance measurement to the offset impedance to determine a change relative to a baseline. The sensor controller 150 may also monitor changes in a series of impedance measurements taken over a period of time, e.g., as a sensed impedance changes while a user's finger is moving towards the selected electrode(s).

Figure 10:
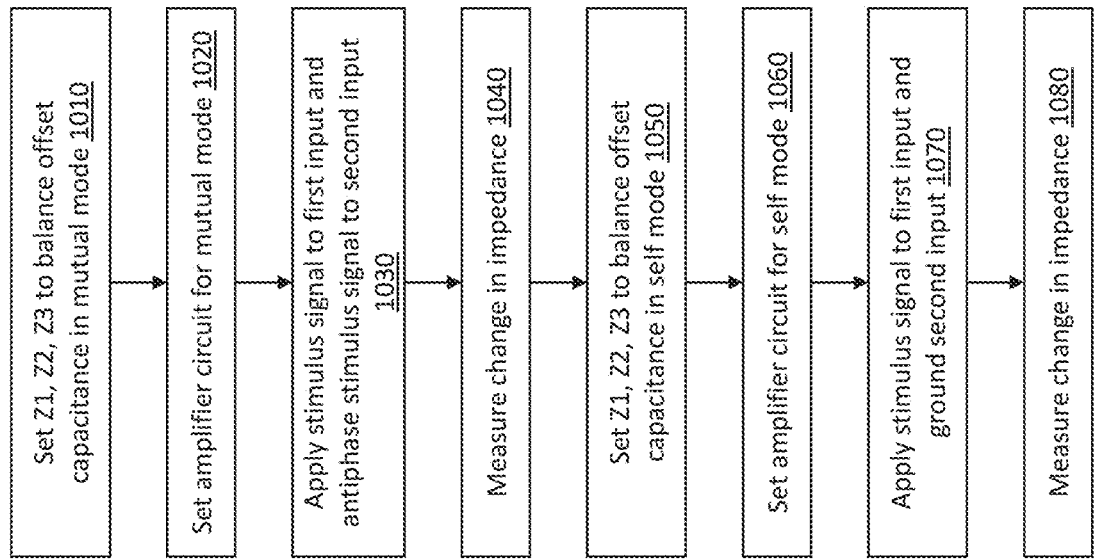
FIG. 10 provides a method for using a sensor system in both a mutual-sensing mode and a self-sensing mode, according to some embodiments of the present disclosure.

FIG. 10 provides a method for using an impedance sensor in both a mutual-sensing mode and a self-sensing mode, according to some embodiments of the present disclosure. The sensor, e.g., the sensor controller 150, sets 1010 impedances Z1, Z2, and Z3 to balance an offset impedance in mutual-sensing mode. In particular, the sensor controller 150 sets one or more of the impedances Z1, Z2, and Z3 for a particular set of electrodes configured for the mutual-sensing mode. The sensor, e.g., the sensor controller 150, further sets 1020 the configuration of the amplifier circuit 130 for mutual-sensing mode, e.g., in the configuration shown in FIG. 5. The sensor, e.g., the driver circuit 110, applies 1030 a stimulus signal (e.g., the stimulus signal 552 or 752) to a first input to the impedance bridge (e.g., to the first input terminal 525 or 725) and an antiphase stimulus signal (e.g., the stimulus signal 554 or 754) to a second input to the impedance bridge (e.g., to the second input terminal 530 or 730). The sensor measures 1040 a change in impedance across the electrodes coupled to the coupling network of the impedance bridge. For example, the impedance measurement obtained by the sensor controller 150 based on the output of the signal processing circuit 140 indicates a change in impedance relative to the offset impedance.

The sensor, e.g., the sensor controller 150, sets 1050 impedances Z1, Z2, and Z3 to balance an offset impedance in self-sensing mode. In particular, the sensor controller 150 sets one or more of the impedances Z1, Z2, and Z3 for a particular electrode used for sensing in the self-sensing mode. The sensor, e.g., the sensor controller 150, further sets 1060 the configuration of the amplifier circuit 130 for self-sensing mode, e.g., in the configuration shown in FIG. 4. The sensor, e.g., the driver circuit 110, applies 1070 a stimulus signal (e.g., the stimulus signal 452 or 852) to a first input to the impedance bridge (e.g., to the first input terminal 525 or 725). A stimulus signal is not applied to the other side of the impedance bridge; instead, as shown in FIG. 8, the third impedance element is grounded. The sensor measures 1080 a change in impedance sensed by an electrode coupled to the coupling network of the impedance bridge. For example, the impedance measurement obtained by the sensor controller 150 based on the output of the signal processing circuit 140 indicates a change in impedance relative to the offset impedance.

Shaping Electric Fields for Di-Electric Relaxation Measurements

The sensor system described above may be used in the self-sensing configuration as a di-electric relaxation sensor. The sensing impedance element (e.g., a sensing electrode coupled to the coupling network 320) produces an electric field and measures changes to the electric field due to changes in its environment.

Figure 11:
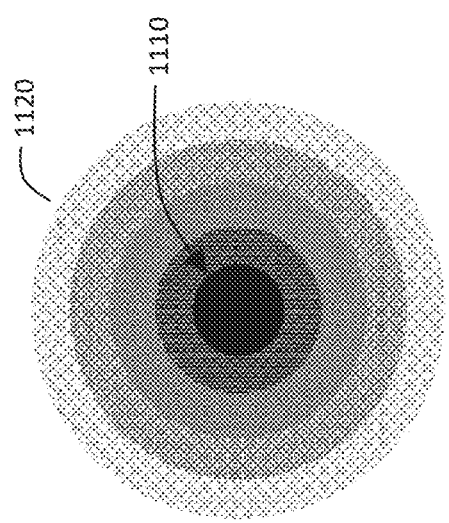
FIG. 11 illustrates an electric field generated by an electrode in a self-sensing impedance sensor, according to some embodiments of the present disclosure.

Di-electric relaxation measurements are inherently an omni-directional measurement of the materials surrounding the electrode. In particular, a di-electric relaxation sensor measures the average di-electric relaxation factor of a sphere surrounding the electrode. FIG. 11 provides a two-dimensional illustration of an electric field 1120 generated by an electrode 1110 coupled to a self-sensing impedance sensor. The variance in field strength as a function of distance from the electrode 1110 also impacts the measurement. This variance is represented through the shading of the concentric circles illustrating the electric field 1120 in FIG. 11; the field strength is weaker (represented as a lighter color) further from the electrode 1110.

The resulting di-electric relaxation factor of the sensor represented in FIG. 11 can be expressed as the sum of the field strength*di-electric relaxation/volume of measurement. For many applications, it is advantageous to direct the measurement in a given direction, rather than taking an omni-directional measurement. Existing sensor systems use a beamforming technique to achieve directionality in the electric field. However, conventional beamforming techniques become challenging for di-electric relaxation sensor systems having small form factors due to the high frequencies used to measure di-electric relaxation.

In particular, the frequency employed to measure di-electric relaxation times can be in the range of frequencies are 10 kHz-1 MHz. These frequencies results in a long wavelength, e.g. 300 m for a 400 kHz frequency. Using conventional beamforming techniques requires the receivers to be spatially far enough apart to be able to resolve a meaningful phase difference. If the receivers are close, e.g. 1 cm apart, the phase difference of an orthogonal, or side, signal will be 1 cm/(300 m*100 cm/m) degrees or 1/30,000 degrees. For a simple delay sum beamformer this will result in ~0 dB attenuation. Thus, beamforming is well suited to systems with multiple receivers placed far apart, but cannot be used in systems with a single receiver, or in small form factor systems.

For smaller form factor systems, the emitted field 1120 can be shaped by field shaping elements rather than using beamforming to shape the field. By shaping the emitted field, field directionality can be achieved without requiring multiple receivers. By contrast, conventional beamforming requires at least two receivers to gain a minimum of 3 dB attenuation.

Figure 12:
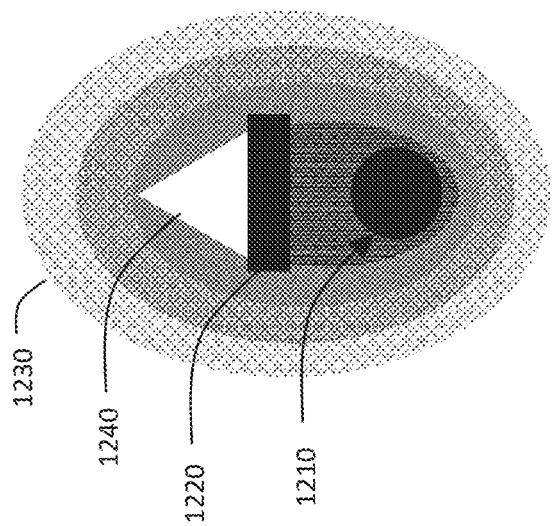
FIG. 12 illustrates an electric field generated by an electrode and shaped by a grounding element, according to some embodiments of the present disclosure.

FIG. 12 illustrates an electric field 1230 generated by an electrode 1210 and shaped by a grounding element 1220, according to some embodiments of the present disclosure. The grounding element 1220 is adjacent to the electrode 1210 and "pulls" the field from the electrode 1210. The ground element 1220 thus distorts the shape of the electric field 1230 to become a more ovaloid shape than the spherical/omni-directional field shown in FIG. 11. In addition, the grounding element creates a shade 1240 behind it. The shade 1240 is a region having little to no electric field strength from the electrode 1210. Because the ground element 1220 "pulls" the electric field 1230, the ground element 1220 also has a decremental effect on the range of the field 1230 opposite the ground element 1220.

Field shaping with a ground electrode 1220 can be used in applications that measure the average di-electric relaxation factor within a given volume. Changing the shape of the emitted field also changes the shape of the volume for which the average di-electric relaxation factor is measured.

In some embodiments, the electric field can be shaped by designing the electrode 1210 and the environment around the electrode such that the field shape is altered from the spherical shape shown in FIG. 11. For example, multiple ground elements can be placed around the electrode 1210 to focus the field strength in a given direction.

Other ground shapes, like half shells, cylinders, etc., may be used instead of or addition to the linear element 1220 shown in FIG. 11. Other ground shapes may distort the field even more, resulting in even higher directionality. The higher the directionality obtained through field shaping, the lower the field strength emitted will be, which lowers the sensing capability of the directed sensor. However, the lowering in field strength by increasing directionality can, at least in part, be combated by increasing the strength of the field. Note that in addition to increasing power usage, increasing the field strength will cause simple field distortions, like the one shown in FIG. 12, to become less efficient.

Shaping the emitted field achieves a form of directionality akin to beam forming. Directed sensors can be used to effectively improve the di-electric relaxation factor measurement for various applications. For example, a directed sensor can be used in forward sensing systems, by directing the electric field out of a given device (e.g., a cell phone for hand or face detection). As another example, directed sensors can be used for gesture or grip sensing. Example applications of gesture and grip sensing include VR wands that measure finger position and grip strength; cell phones that measure finger position and grip strength; or virtual buttons or sliders in various user interfaces. In such embodiments, the reduced range of the electric field caused by the ground elements is beneficial, as the reduced range makes it easier to distinguish desired signals from undesired signals, or to avoid detection of undesired signals.

Sensing In-Ear Placement of Earphones

In some headsets, particularly wireless headsets, determining whether a headset has been inserted into an ear and/or over a user's head is used to control the on/off function of the device. For example, when a headset senses that it has been placed in a user's ear, the headset turns on, and when the headset senses that it has been removed from the user's ear, or has been removed for a threshold length of time, the headset turns off. This allows longer battery life versus using other stimulus to turn the headset on and off, e.g. Bluetooth activity to determine usage, or a user-controlled on-off switch.

Current methods for determining whether a headset has been placed in a user's ear or on a user's head include using optical measurements, capacitive measurements, or bio-impedance measurements. Each of these methods have drawbacks. Optical solutions rely either measuring lack of ambient light, typically infrared light, or measuring reflection of emitted light. These solutions can easily be fooled by non-ear enclosures, e.g., a user's hand, pocket, or bag. Capacitive measurements can work better than optical solutions at distinguishing ears from other enclosures, but still struggle to differentiate between an ear and other body parts, e.g., a hand, a finger, etc. Bio-impedance, like the capacitive measurements, suffer from lack of discernibility between human skin in the ear and everywhere else on the human body.

To better differentiate between a human ear and other enclosures or body parts, a headset can include the sensor system described above to obtain di-electric relaxation measurements, which can be used to determine the properties of the tissue surrounding the headset. For example, di-electric relaxation measurements can be used to distinguish the volume of human tissue that forms a human ear canal from the volume of tissue that would constitute an open, or closed, hand. The sensor can also determine whether it is in a space having a non-tissue material between the headset any human tissue, e.g., in a pants pocket.

Figure 13:
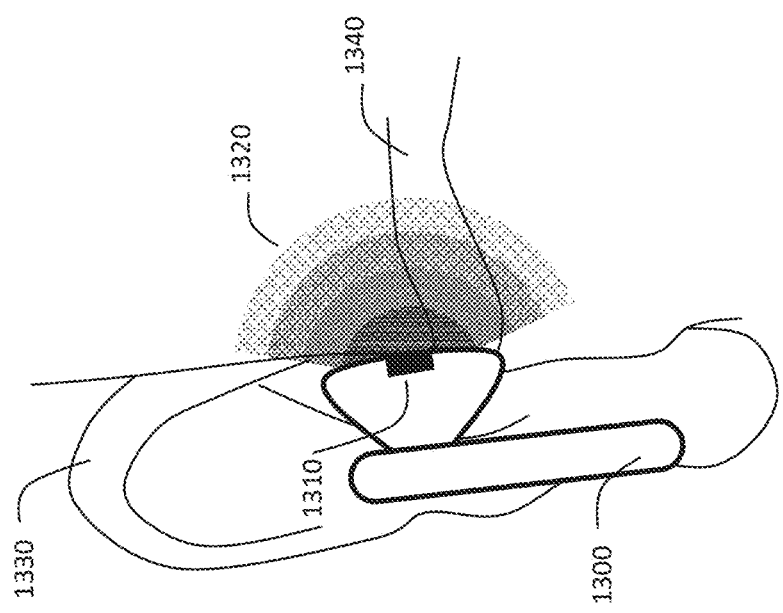
FIG. 13 illustrates an earphone with an integrated impedance sensor positioned in a user's ear, according to some embodiments of the present disclosure.

FIG. 13 illustrates an earphone 1300 with an integrated impedance sensor positioned in a user's ear 1330, according to some embodiments of the present disclosure. The earphone 1300 may be a wireless earphone. The earphone 1300 includes a sensor system, e.g., the sensor system 100 described above. The sensor system includes an impedance bridge, which may be arranged in the self-sensing configuration described with respect to FIGS. 4 and 8 or the mutual-sensing configuration described with respect to FIGS. 5 and 7, or may alternate between the two configurations. The sensor system is driven by a driver circuit, e.g., the driver circuit 110. The sensor system includes a sensing element 1310 (e.g., an electrode or a pair of electrodes) for generating and sensing an electric field 1320, and in particular, to sense an impedance response in an environment of the sensing element 1310. The sensor system includes circuitry, such as the amplifier circuit 130, signal processing circuit 140, and sensor controller 150, to receive an output of the impedance bridge via its output terminals, determine a position of the earphone 1300 based on the output of the impedance bridge (e.g., in the user's ear 1330 or not), and alter a behavior of the earphone 1300 based on the determined position (e.g., by turning an audio function of the earphone 1300 on when the earphone 1300 is in the user's ear, and turning an audio function of the earphone 1300 off when the earphone 1300 is not in the user's ear).

Figure 14A:
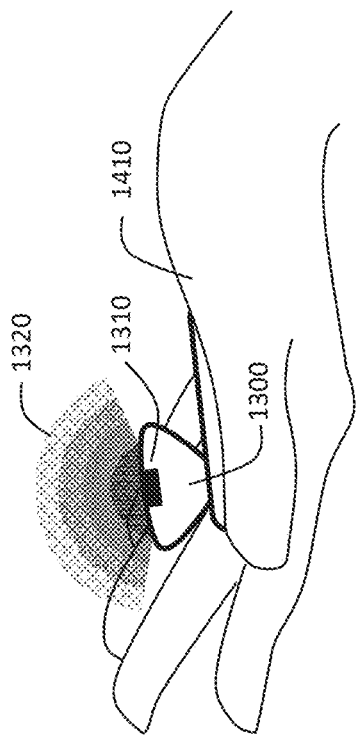
FIGS. 14A and 14B illustrate the earphone of FIG. 13 in two positions within a user's hand, according to some embodiments of the present disclosure.

FIG. 13 shows the position of the earphone 1300 in a user's ear 1330. FIGS. 14A and B show the position of the same earphone 1300 in two different positions within the user's hand 1410. The sensor measures the electric field strength in the environment of the sensing element 1310; the electric field strength corresponds to the relative permittivity of the materials in the region of the electric field. The sensor may further include one or more ground elements for shaping the electric field 1320. As shown in FIG. 13, when the earphone 1300 is positioned in the user's ear 1330, the electric field 1320 is directed out of the earphone 1300 in the direction of the user's head.

Figure 14B:
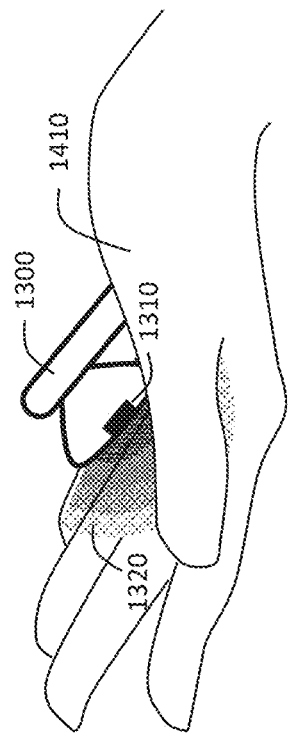

The sensor system uses a measurement of the electric field 1320 to determine the volume of human tissue surrounding the earphone 1300. When the earphone 1300 is positioned in the user's ear 1330, the electric field 1320 extends through a portion of the user's head and into the user's ear canal 1340. When the earphone 1300 is positioned in the user's hand 1410 as shown in FIG. 14A, the electric field 1320 extends upwards into the air, so the electric field 1320 extends through less human tissue than in FIG. 13. When the earphone 1300 is positioned in the user's hand 1410 as shown in FIG. 14B, the electric field 1320 extends into the user's hand 1410, so volume of human tissue reached by the electric field 1320 is greater in FIG. 14B than in FIG. 13. In addition, the composition of the human tissue surrounding the ear 1330 is different from the human tissue in the hand, which leads to different di-electric permittivity measurements. The di-electric relaxation sensor in the earphone 1300 thus measures a different relative permittivity in the in-ear environment than in the hand environments. This allows the earphone 1300 (e.g., a controller in the earphone 1300 connected to the sensing element 1310) to correctly determine whether the earphone 1300 has been placed in the user's ear 1330 or the user's hand 1410, based on the measured permittivity.

In a similar fashion, the sensor system can be used to differentiate between other scenarios, such as in a pocket, in the user's fingers, in a bag, etc., because the sensor system can be tuned to the unique structure of the human ear and ear canal.

Sensing Material Properties with Impedance Sensor

In various applications it is beneficial to determine what materials are around a given device. For example, for a cellphone, it is useful to know if the cellphone has been placed on a table (e.g., a glass, wood, or steel surface), in a user's pocket, or in a bag (e.g., a cloth or leather enclosure). As another example, for adaptive speaker systems, it is beneficial to know what materials the bass speaker is placed on and is using for reflection. A lack of environmental recognition makes it challenging for such devices to properly adapt to their conditions, e.g., to utilize information about the environment to tune or otherwise change the behavior of a product to adapt to the surrounding environment.

In a typical adaptive speaker, a woofer, or full-tone, speaker emits sound downwards, typically onto a spreader cone. A challenge with these setups is the reflections from the material underneath the speaker unit. In some previous adaptive speakers, a long-term acoustic measurement is performed to determine the overall room properties. Using an acoustic sensor at the bottom of the unit, the adaptive speaker can obtain an acoustic measurement and determine what material (e.g. a shelf) on which the speaker has been placed is constructed from. This allows the speaker to adapt to the acoustic properties of the environment below the unit. In some prior implementations, a second acoustic sensor is placed around the speaker unit to determine whether the speaker is placed in an "open" acoustic environment or whether one or more sides of the speaker is facing a wall or other obstructing object. Determining if there is obstruction around the speaker unit, and where it is, allows the adaptive speaker to tune the echo canceller and beamforming included in a smart speaker system. The challenge faced using sound to measure the location of walls and other objects within a room is that such objects are inherently near field and can be a challenge to detect.

FIG. 15 illustrates a speaker 1510 with an integrated impedance sensor positioned on a table 1540, according to some embodiments of the present disclosure. The sensor can obtain and utilize di-electric relaxation measurements to measure the average relative permittivity of the environment around the sensor. The speaker 1510 includes a sensor system, e.g., the sensor system 100 described above. The sensor system includes an impedance bridge, which may be arranged in the self-sensing configuration described with respect to FIGS. 4 and 8 or the mutual-sensing configuration described with respect to FIGS. 5 and 7, or may alternate between the two configurations. The sensor system is driven by a driver circuit, e.g., the driver circuit 110. The sensor system includes a sensing element 1520 (e.g., an electrode or a pair of electrodes) for generating and sensing an electric field 1530, and in particular, to sense an impedance response in an environment of the sensing element 1530. The sensor system includes circuitry, such as the amplifier circuit 130, signal processing circuit 140, and sensor controller 150, to receive an output of the impedance bridge via its output terminals and to measure a relative permittivity in an environment of the sensing element 1520 based on the output of the impedance bridge.

The sensor measures the electric field strength in the environment of the sensing element 1520; the electric field strength corresponds to the relative permittivity of the materials in the region of the electric field. The sensor may further include one or more ground elements for shaping the electric field 1530. As shown in FIG. 15, when the speaker 1510 is positioned on the table 1540, the electric field 1530 is directed out of the base of the speaker 1510 and into the table 1540. Additional or alternate sensor systems may be placed in other locations in the speaker 1510 to identify materials in other directions.

The example table 1540 includes a material stack of three different materials. FIG. 16 illustrates a cross-section of the speaker 1510 and the table 1540, showing the three layers, 1610, 1620, and 1630. In one example, the first layer 1610 is wood, the second layer 1620 is glass, and the third layer 1630 is steel. In other examples, different numbers of layers and different types and combinations of materials may be present. Each of the layers 1610, 1620, and 1630 may have a different relative permittivity. For example, wood has a relative permittivity between 2 and 4, glass has a relative permittivity between 5 and 10, and steel has an infinite permittivity, in that it blocks an electric field. Furthermore, for certain materials, the relative permittivity varies based on the frequency of the electric field, i.e., the frequency of the stimulus signal generated by the driver circuit 110.

For a given individual stack of materials, it is feasible to determine the composition of the stack by measuring the average relative permittivity of the stack and using the following formula, where Er(material) is the relative permittivity of each individual material:

$$\text{avg\_relative\_permittivity} = \text{sum\_over\_volume}(\text{field strength} * Er(\text{material}))$$

From the measured permittivity it is possible to initially estimate the composition of the material stack as a ratio of detectable materials. The accuracy of this estimate can be improved by performing measurements at more than one frequency, as the relative permittivity of the various materials derate differently versus the excitation frequency, i.e., materials have different responses in relative permittivity across a range of excitation frequencies. More particularly, the permittivity of a material typically decreases as the frequency of the electric field increases. In addition, the permittivity falls with increasing temperature. These factors can be taken into account when analyzing the measured permittivity.

The quality of the estimate can be further improved by training a classifier, e.g. a classifier based on a neural network, by exposing the sensor to various types of detectable materials in various combinations from various angles at various frequencies, and using the measurements collected by the sensor to train the neural network. The classifier is trained to identify the material in the environment of the sensing element 1520. The estimates can further be improved by calibrating the sensor to a "base" environment that equates the devices in which the sensor is located with the devices suspended inside an "empty" environment. Calibration this way allows us to remove the device in which the sensor is embedded from our sensing, effectively making the device containing the sensor "invisible" to our sensor.

The material classification sensor can be used for other applications besides the smart speaker example, such as altering behavior of a smartphone, cell phone, or other similar device based on materials around the device. For a smartphone, a challenge is understanding the environment surrounding the smartphone, e.g. whether the smartphone is in a pocket, on a table, etc. By determining information about its surrounding environment, the smartphone can change its behavior depending on the environment.

For example, using the sensor system 100 in a smartphone resting on a flat surface allows the smartphone to determine which side is facing up, and which side is facing the surface. Based on the determination of which side is up, the smartphone may change its speaker behavior in speaker phone mode, and determine how to indicate to a user various events happening (such as showing a display, vibrating, and/or ringing in response to an incoming call), among other behaviors. In a similar fashion, determining whether the smartphone is in an enclosure like a pocket or a bag also allows the smartphone to change behavior, e.g., to emit a stronger vibration but no sound when the smartphone is in a pocket, or to not vibrate but emit a louder sound, when the smartphone is in a bag.

Figure 17:
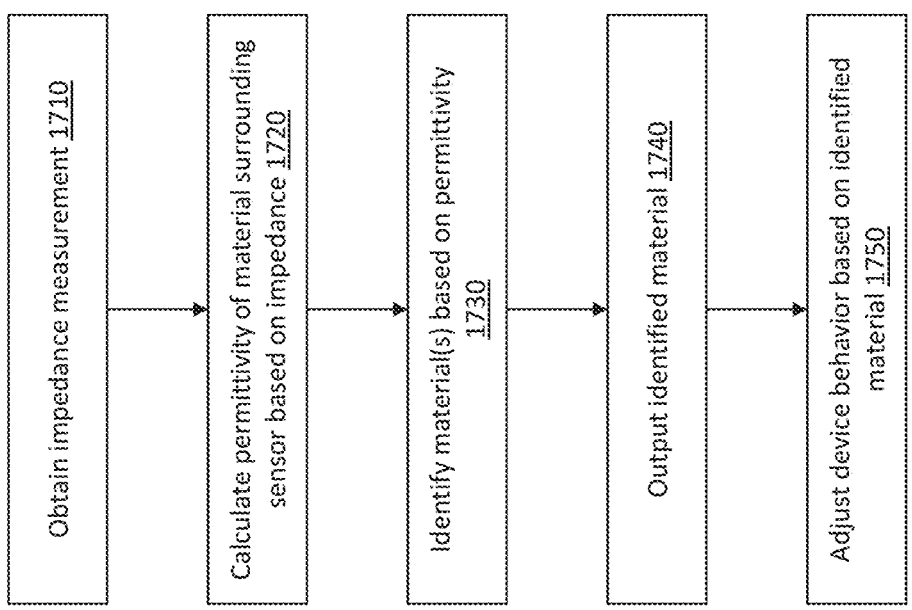
FIG. 17 provides a method for adjusting behavior of an electronic device based on permittivity of an environment around an impedance sensor integrated into the electronic device, according to some embodiments of the present disclosure.

FIG. 17 provides a method for adjusting behavior of an electronic device based on permittivity of an environment around an impedance sensor integrated into the electronic device, according to some embodiments of the present disclosure. The sensor system, e.g., the sensor system 100, obtains 1710 an impedance measurement, as described in detail above. The sensor system, e.g., the sensor controller 150, calculates 1720 permittivity of the material surrounding the sensor (e.g., the table 1540 under the sensing element 1520) based on the impedance measurement or a series of measurements, e.g., measurements obtained for stimulus signals at different frequencies. The sensor system, e.g., the sensor controller 150, identifies 1730 the material or materials in the environment of the sensor based on the permittivity. For example, the sensor controller 150 uses a classifier trained to identify a material or set of materials based on a measurement or series of measurements. The sensor system outputs 1740 the identified material, e.g., to control circuitry for a device into which the sensor system 100 is integrated. For example, the sensor system outputs data identifying the stack of materials 1610, 1620, and 1630 in the table 1540 to a processor controlling the adaptable speaker 1510. The device alters 1750 its behavior based on the identified materials. For example, the speaker 1510 alters audio settings based on the identified tabletop materials. As another example, a smartphone alters notifications, alert settings, audio settings, etc. based on whether the smartphone is positioned face-up or face-down on a table.

Sensing Organic Tissue Properties With Impedance Sensor

For many medical applications, it is beneficial to know the type of tissue is around a given medical device, e.g. as an immersion probe, or the type of tissue in front of a given medical device, e.g. as a tissue scanner. Existing methods of determining types of tissue and certain properties of tissue include invasive extraction, tissue sampling, expensive imaging equipment (e.g. x-ray or MRI), and visual inspection by training physicians or surgeons. Using these methods, various properties can be determined, such as type of tissue, health of the tissue, or whether there are cancerous growths in or around the tissue. However, most of the existing methods are invasive, prone to error, expensive, and/or can take a lot of time to obtain a diagnosis.

One prior method for ascertaining whether a cancerous growth has occurred involves first determining whether there is a likelihood of cancer by touch (firm/not firm tissue), pain, discoloration (red/not-red), imaging (x-ray, MRI), or behavior changes (mood, body temperature, speech impediments, etc.), or some other method. After determining that there is a likely cancerous growth, the next step is taking a tissue sample, i.e., a biopsy, from the area in question. The sample is then typically inspected optically, to determine whether there is any abnormal growth, and if there is, if said abnormal growth is cancerous or not.

One existing method for removing cancer is by surgically cutting out the growth. This followed by post-op treatments (e.g., radiation, chemotherapy) to prevent any missed cancerous tissue from causing a regrowth of the cancerous tissue. During a standard surgical procedure, surgeons often remove excess tissue around a given cancerous growth to ensure that no cancerous tissue is missed. Various cancer types have various best-in-class methods for surgical treatment, and not all cancers are treated the same. In some cases, such as skin cancer removal, it can be problematic to remove "too much" tissue. To avoid this, surgeons try to determine the extent of the cancerous area by ways of touch and by observing skin discoloration. The surgeon goes through a sequence of cutting away suspected cancerous tissue followed by optically inspecting the fringes of the cut tissue to determine whether there is enough distance from cancerous tissue to the edge. The surgeon will then repeat the cutting and inspection until it is determined that there is enough clearance. This method of repeated surgical removal, followed by optical inspected, and follow-up removal is currently a standard process, but it can be stressful for the patient. Nonvisible cancers are imaged using various imaging techniques, such as computed tomography (CT) or magnetic resonance imaging (MRI) scanning techniques. These imaging techniques are very powerful, but also quite time-consuming and expensive.

A di-electric relaxation sensor can be used to identify tissue properties, e.g., to distinguish between cancerous and non-cancerous tissues, in a way that is both fast and non-invasive. Previous sensors have been used to determine tissue type by measuring relative permittivity, but such sensors typically use either very low frequencies (<1 kHz) or very high frequencies (>1 Ghz). For example, high frequency sensors have been used for determining impacts of RF exposure.

In particular, the impedance sensor described above, e.g., sensor system 100, is used to scan tissues and determine the relative permittivity of the tissues, which can be used to determine a type of tissue and/or distinguish between different types of tissue. The sensor can obtain and utilize di-electric relaxation measurements to measure the relative permittivity of the environment around the sensor. The sensor system includes an impedance bridge, which may be arranged in the self-sensing configuration described with respect to FIGS. 4 and 8 or the mutual-sensing configuration described with respect to FIGS. 5 and 7, or may alternate between the two configurations. The sensor system is driven by a driver circuit, e.g., the driver circuit 110. The sensor system includes a sensing element (e.g., an electrode or a pair of electrodes) for generating and sensing an electric field, and in particular, to sense an impedance response in an environment of the sensing element. The sensor system includes circuitry, such as the amplifier circuit 130, signal processing circuit 140, and sensor controller 150, to receive an output of the impedance bridge via its output terminals and to measure a relative permittivity in an environment of the sensing element based on the output of the impedance bridge. In some embodiments, the sensor controller 150 is further configured to classify a tissue as a particular tissue type, or classify a tissue as being cancerous or non-cancerous, based on the measured relative permittivity.

It has been shown that relative permittivity measurements can be used to distinguish various tissues from each other. For example, blood typically has a higher relative permittivity than liver, which has a higher relative permittivity than brain, which has a higher relative permittivity than fat. Furthermore, the measured relative permittivity of tissue is frequency-dependent, with lower frequencies producing a greater relative permittivity response. Furthermore, the rate of change in relative permittivity as a function of frequency is tissue-dependent.

The sensor system described above may be used to measure the relative permittivity of the volume surrounding the sensor, and this measurement is used to estimate the mix of materials, as described with respect to FIGS. 15 and 16. For the tissue sensing application, rather than using the sensor system to identify a combination of environmental materials, such as wood and metal, the sensor system can be used to measure different tissue compositions. For example, a classifier can be trained to identify various combinations of tissues by exposing the sensor to various types of detectable materials in various combinations from various angles at various frequencies, and using the collected measurements to train a neural network.

The sensor system is able to measure at more than one frequency, including frequencies in the range of 100 kHz to 1 MHz. Lower and higher frequencies are also feasible for the sensor. Unlike prior sensors for measuring relative permittivity, the sensor system disclosed herein is not limited to using either very low or very high frequencies. As biological tissue (unlike organic tissue) has distinct frequency-based degradation based on tissue type, using the sensor system at multiple frequencies improves its ability to recognized different tissues by taking measurements of electric fields at multiple frequencies. This additional information improves the sensor's ability to determine the mix of tissues around the sensor itself. Adding in directionality, as described with respect to FIGS. 11 and 12, further improves recognition, as the sensor can filter unwanted sensing directions from the measurement.

The capacitance measurements obtained by the sensor system can be used to distinguish cancerous from non-cancerous tissues. Capacitance is correlated to the di-electric relaxation measurement obtained by the sensor system. The sensor system is highly sensitive, capable of measuring capacitances on the order of ~1 aF ($10^{-18}$ F), which is sensitive enough to detect cancerous cells. The sensor system may also be able to determine a ratio of normal versus cancerous tissue.

In one particular example application, the sensor system is used to measure cancerous versus non-cancerous tissue in a brain, based on the frequency dependency of relative permittivity of normal versus cancerous brain tissue. The relative permittivity of cancerous cells have a different frequency response than normal brain cells. This is can be determined to be caused by the composition of cancerous variants of a given tissue. A further aspect of the frequency dependence of cancerous cells is a link between the stage of the cancer cells and the peak relative permittivity. In particular, it has been shown that the peak frequency moves based on the size of the cancer cluster, the stage of the cancer also causes the peak frequency to move.

As described above, the sensor system can emit electric field across a range of frequencies; in particular, the sensor can sweep the field frequency with high accuracy. For example, the driver circuit 110 can adjust the frequency of the field generated by the electrode(s) coupled to the impedance bridge in steps of <500 Hz. Having a fine-grained control of the field frequency is important to accurately determine not only the stage of a given cancer cluster, but also its size/radius.

The sensor system can scan tissues either directly (e.g., by positioning the sensor in or on a patient's body), or scan tissues in a solution. The sensor system may be integrated into an insertable sensor or injectable device for accessing different parts of the body. The sensor system can determine what type of tissue or tissues are present in the sample based on a measurement or series of measurements, e.g., a series of measurements obtained using a sequence of stimulus signals at different frequencies. The sensor system may determine whether there are any abnormalities in the sample (e.g., cancerous tissue) based on the measurements, and may further determine a type of abnormality (e.g., a stage of cancer) based on the measurements. The sensor system may adjust the depth of a scan by generating stimulus signals at different amplitudes, which generate different electric field strengths. A higher amplitude stimulus signal generates an electric field that extends into a larger volume of tissue for deeper or wider-range sensing, and a lower amplitude stimulus signal generates an electric field that extends into a smaller volume of tissue for more localized sensing. One or more grounding elements may be used to shape the field, as described with respect to FIGS. 11 and 12.

Figure 18:
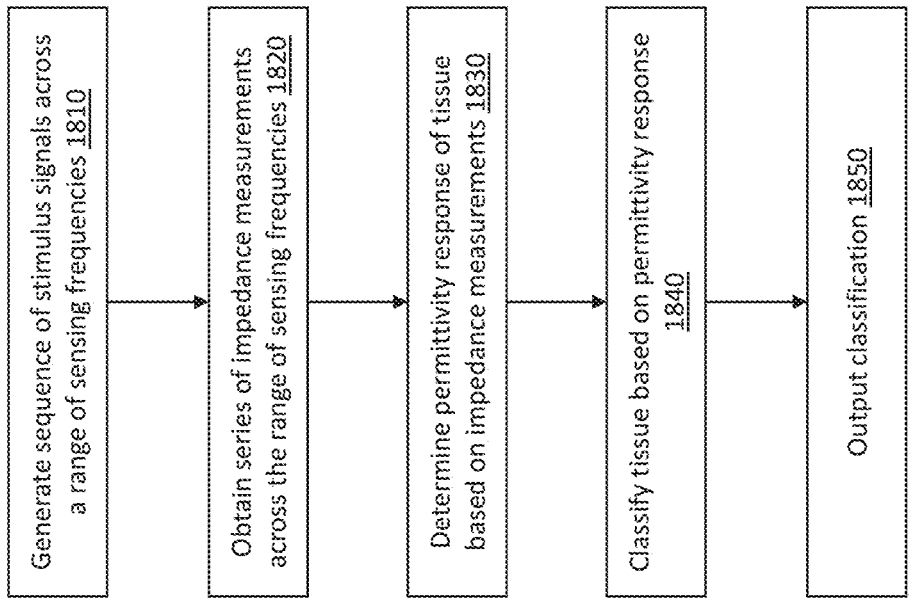
FIG. 18 provides a method for classifying a tissue based on permittivity of the tissue, according to some embodiments of the present disclosure.

FIG. 18 provides a method for classifying a tissue based on permittivity of the tissue, according to some embodiments of the present disclosure. A tissue sensor system, e.g., the driver circuit 110 of the sensor system 100, generates 1810 a sequence of stimulus signals across a range of sensing frequencies. The sensor system obtains 1820 a series of impedance measurements across the range of sensing frequencies. The sensor system determines 1830 the permittivity response of a material surrounding the sensor based on the impedance measurements. For example, the sensor controller 150 determines a series of relative permittivity measurements each associated with a particular excitation frequency. As noted above, the repeated excitation of the tissue with stimulus fields of different frequencies can influence the relative permittivity measurements obtained. The sensor system classifies 1840 the tissue based on the permittivity response. The sensor system may use a machine learning classifier trained based on relative permittivity responses of a set of sample tissues. The sensor system output 1850 the classification. The classification may be used in real-time, e.g., during surgery or biopsy, to guide a doctor using the sensor.

Select Examples

Example 1 provides a sensing circuit that includes an input terminal; a first impedance element coupled between the input terminal and a first output terminal, where the first impedance element is a variable impedance element; a second impedance element coupled between the input terminal and a second output terminal; a third impedance element coupled to the second output terminal; a coupling network coupled to the first output terminal; and an amplifier circuit coupled to the first output terminal and the second output terminal, the amplifier circuit to output a voltage related to an environmental characteristic sensed by a sensing impedance element coupled to the coupling network.

Example 2 provides the sensing circuit according to example 1, the sensing circuit further including circuitry to adjust an impedance of the first impedance element to balance an offset impedance on the sensing impedance element.

Example 3 provides the sensing circuit according to example 1 or 2, where the second impedance element is a variable impedance element.

Example 4 provides the sensing circuit according to example 3, the sensing circuit further including circuitry to determine, based on an offset impedance, a first impedance for the first impedance element; and determine a second impedance for the second impedance element based on the offset impedance and the first impedance, where a first impedance ratio between the second impedance and a third impedance of the third impedance element is equal to a second impedance ratio between the first impedance and the offset impedance.

Example 5 provides the sensing circuit according to example 4, where the first impedance and second impedance belong to a first set of impedances for a first sensing mode, and the circuitry is further configured to determine a second set of impedances for the first and second impedance elements for a second sensing mode.

Example 6 provides the sensing circuit according to any of the preceding examples, the sensing circuit further including a driver circuit to generate a stimulus signal, adjust a frequency of the stimulus signal, and apply the stimulus signal at the input terminal.

Example 7 provides the sensing circuit according to example 6, where the driver circuit is configured to apply a plurality of stimulus signals to the input terminal, and each of the plurality of stimulus signals has a different frequency.

Example 8 provide the sensing circuit according to example 6 or 7, the sensing circuit further including a signal processing circuit to correlate the stimulus signal with an output of the amplifier circuit, the signal processing circuit coupled to the amplifier circuit and coupled to the driver circuit.

Example 9 provides the sensing circuit according to any of the preceding examples, where each of the first, second, and third impedance elements includes a capacitor and a resistor in series.

Example 10 provides the sensing circuit according to any of the preceding examples, where the first and second impedance elements each include a capacitor and a pullup resistor arranged in parallel with the capacitor.

Example 11 provides the sensing circuit according to any of the preceding examples, where the coupling network is coupled to a ground.

Example 12 provides the sensing circuit according to example 11, where the third impedance element is coupled between the second output terminal and the ground.

Example 13 provides the sensing circuit according to any of the preceding examples, the sensing circuit further including a second input terminal coupled to the coupling network.

Example 14 provides the sensing circuit according to example 13, where the third impedance element is coupled between the second output terminal and the second input terminal.

Example 15 provides a sensor system that includes a driver circuit to generate a periodic stimulus signal; an impedance bridge including a first impedance element, a second impedance element, and a third impedance element, where the first impedance element is a variable impedance element; an input terminal coupled to the driver circuit and coupled to the impedance bridge to apply the stimulus signal to the impedance bridge; a coupling network coupled to a first output terminal of the impedance bridge; and an amplifier circuit coupled to the first output terminal and a second output terminal of the impedance bridge, the amplifier circuit configured to output a voltage based on signals from the first output terminal and the second output terminal.

Example 16 provides the sensor system according to example 15, the sensor system further including circuitry to adjust an impedance of the first impedance element to balance an offset impedance on a sensing impedance element coupled to the coupling network.

Example 17 provides the sensor system according to example 15 or 16, where the second impedance element is a variable impedance element, and the sensor system further includes circuitry to determine, based on an offset impedance, a first impedance for the first impedance element; and determine a second impedance for the second impedance element based on the offset impedance and the first impedance, where a first impedance ratio between the second impedance and a third impedance of the third impedance element is equal to a second impedance ratio between the first impedance and the offset impedance.

Example 18 provides the sensor system according to any of examples 15 through 17, where the driver circuit is configured to generate a plurality of periodic stimulus signals each having a respective frequency and to apply the plurality of periodic stimulus signals to the input terminal.

Example 19 provides the sensor system according to any of examples 15 through 18, the sensor system further including a signal processing circuit to correlate the periodic stimulus signal with an output of the amplifier circuit, the signal processing circuit coupled to the amplifier circuit and coupled to the driver circuit.

Example 20 provides the sensor system according to any of examples 15 through 19, where each of the first, second, and third impedance elements includes a capacitor and a resistor in series.

Example 21 provides a method for detecting a change in an environment characteristic, the method including determining, based on an offset impedance, a first impedance for a first impedance element arranged with a second impedance element and third impedance element as an impedance bridge; configuring the first impedance element according to the determined first impedance; applying a periodic stimulus signal to the impedance bridge; and receiving an output of the impedance bridge via a first output terminal and a second output terminal.

Example 22 provides the method according to example 21, the method further including determining a first impedance ratio between the first impedance and the offset impedance; and determining a second impedance for the second impedance element based on the first impedance ratio, where a second impedance ratio between the second impedance and a third impedance of the third impedance element is equal to the first impedance ratio.

Example 23 provides the method according to example 22, where the first impedance and second impedance belong to a first set of impedances for a first sensing mode, and the method further includes determining a second set of impedances for the first and second impedance elements for a second sensing mode, the second set of impedances based on a second offset impedance for the second sensing mode.

Example 24 provides the method according to any of examples 21 through 23, the method further including receiving, at an amplifier circuit, a first signal from the first output terminal and a second signal from the second output terminal; amplifying a voltage difference between the first signal and the second signal; and converting the voltage difference to a digital output signal.

Example 25 provides the method according to any of examples 21 through 24, the method further including receiving, at a signal processing circuit, the output of the impedance bridge and the periodic stimulus signal; and correlating the periodic stimulus signal with output of the impedance bridge.

Example 26 provides the method according to any of examples 21 through 25, where the output of the impedance bridge is a first output obtained at a first time, and the method further includes applying a second periodic stimulus signal to the impedance bridge at a second time; receiving a second output of the impedance bridge via the first output terminal and the second output terminal; and determining a change in a sensed impedance from the first time to the second time, the change in the sensed impedance related to a change in an environmental characteristic sensed by a sensing impedance element.

Example 27 provides a sensor system that includes an impedance bridge including a first impedance element, a second impedance element, a third impedance element, and a coupling network arranged in a bridge configuration; a first input terminal coupled to the first impedance element and the second impedance element and configured to apply a first stimulus signal to the impedance bridge; a second input terminal coupled, in a first mode, to the coupling network and the third impedance element to apply a second stimulus signal to the impedance bridge; and at least one switch coupled to the second input terminal, the at least one switch controllable to decouple the second stimulus signal from the coupling network and the third impedance element in a second mode.

Example 28 provides the sensor system according to example 27, where the coupling network includes an electrode switch matrix couplable to a plurality of electrodes, the plurality of electrodes including at least two sensing electrodes.

Example 29 provides the sensor system according to example 28, where in the first mode, the electrode switch matrix is coupled to a first sensing electrode and a second sensing electrode, and an output of the impedance bridge is correlated to a change in capacitance between the first sensing electrode and the second sensing electrode.

Example 30 provides the sensor system according to example 27 or 28, where in the second mode, the electrode switch matrix is coupled to one of the sensing electrodes, and an output of the impedance bridge is correlated to a change in an electric field in an environment of the sensing electrode.

Example 31 provides the sensor system according to any of examples 28 through 30, the sensor system further including circuitry to select an electrode from the plurality of electrodes, and instruct the electrode switch matrix to couple a terminal of the coupling network to a pin corresponding to the selected electrode.

Example 32 provides the sensor system according to any of examples 27 through 31, the sensor system further including a driver circuit to apply the first stimulus signal to the first input terminal in the first mode.

Example 33 provides the sensor system according to any of examples 27 through 32, the sensor system further including a driver circuit to apply, in the second mode, the first stimulus signal to the first input terminal and the second stimulus signal to the second input terminal, the second stimulus signal having opposite phase of the first stimulus signal.

Example 34 provides the sensor system according to any of examples 27 through 33, the sensor system further including a driver circuit to generate a first stimulus waveform having a first frequency in the first mode, and a second stimulus waveform having a second frequency in the second mode.

Example 35 provides the sensor system according to any of examples 27 through 34, where the first impedance element and the second impedance element are variable impedance elements.

Example 36 provides the sensor system according to any of examples 27 through 35, the sensor system further including an amplifier circuit reconfigurable between the first mode and the second mode, the amplifier circuit in the first mode including a first stage to convert a charge between a first output terminal and a second output terminal to a voltage, and a second stage to amplify a voltage difference between an output of the first stage and the first output terminal.

Example 37 provides the sensor system according to any of examples 27 through 36, the sensor system further including an amplifier circuit reconfigurable between the first mode and the second mode, the amplifier circuit including, in the second mode, at least one fully differential amplifier to amplify a voltage difference between a first output terminal of the impedance bridge and a second output terminal of the impedance bridge.

Example 38 provides the sensor system according to any of examples 27 through 37, the sensor system further including a driver circuit to generate the first stimulus signal and the second stimulus signal at a plurality of frequency settings, and circuitry to select one of the plurality of frequency settings for the driver circuit.

Example 39 provides the sensor system according to any of examples 27 through 38, the sensor system further including circuitry to select one of the first mode and the second mode.

Example 40 provides the sensor system according to any of examples 27 through 39, the sensor system further including an amplifier circuit having a plurality of gain settings and circuitry to select a gain setting for the amplifier circuit.

Example 41 provides the sensor system according to any of examples 27 through 40, the sensor system further including circuitry to instruct the sensor system to obtain a sequence of measurements at a sequence of different sensor settings, the sensor settings including at least one of sensor mode, stimulus signal frequency, stimulus signal amplitude, and electrode selection.

Example 42 provides a method for sensing impedance that includes receiving a first instruction to configure a sensor in a first mode, the sensor system including a first impedance element, a second impedance element, a third impedance element, and a coupling network arranged in a bridge configuration; in response to the first instruction, coupling the coupling network to a first electrode and a second electrode; receiving a second instruction to configure the sensor in a second mode; and in response to the second instruction, decoupling the coupling network from the second electrode.

Example 43 provides the method according to example 42, the method further including in response to the first instruction, applying a first stimulus signal to a first input coupled to the first impedance element and the second impedance element, and applying a second stimulus signal to a second input coupled to the coupling network and the third impedance element; and in response to the second instruction, decoupling the second stimulus signal from the coupling network and the third impedance element.

Example 44 provides the method according to example 43, the method further including applying a third stimulus signal to the first input in response to the second instruction, the third stimulus signal having a different frequency from the first stimulus signal/

Example 45 provides the method according to any of examples 42 through 44, the method further including adjusting an impedance setting of least one of the first impedance element and the second impedance element in response to the second instruction.

Example 46 provides the method according to any of examples 42 through 45, the method further including performing a calibration procedure that includes determining a first set of impedances for the first, second, and third impedance elements based on a first offset impedance for the first mode, and determining a second set of impedances for the first, second, and third impedance elements based on a second offset impedance for the second mode, where at least one of the second set of impedances is different from at least one of the first set of impedances.

Example 47 provides a sensor system that includes an impedance bridge including a first impedance element, a second impedance element, a third impedance element, and a coupling network arranged in a bridge configuration; a driver circuit to generate, in a first mode, a first stimulus signal applied to a first input terminal of the impedance bridge, and to generate, in a second mode, a second stimulus signal and a third stimulus signal having an opposite phase of the second stimulus signal, the second stimulus signal applied to the first input terminal; and at least one switch coupled between the driver circuit and the impedance bridge, the at least one switch controllable to couple the third stimulus signal to the impedance bridge in the second mode.

Example 48 provides the sensor system according to example 47, where the coupling network includes an electrode switch matrix couplable to a plurality of electrodes, the plurality of electrodes includes at least two sensing electrodes, the electrode switch matrix is coupled to one of the sensing electrodes in the first mode, and the electrode switch is coupled to a pair of sensing electrodes in the second mode.

Example 49 provides the sensor system according to example 47 or 48, where the first stimulus signal applied in the first mode has a first frequency, and the second stimulus signal and third stimulus signal applied in the second mode have a second frequency different from the first frequency.

Example 50 provides the sensor system according to any of examples 47 through 49, where the first impedance element and the second impedance element are variable impedance elements.

Example 51 provides the sensor system according to any of examples 47 through 50, the sensor system further including an amplifier circuit reconfigurable between a first configuration and a second configuration, the second configuration including a first stage to amplify a voltage difference between a first output terminal and a second output terminal, and a second stage to amplify a voltage difference between an output of the first stage and the first output terminal.

Example 52 provides a sensor system that includes an impedance bridge including a first impedance element, a second impedance element, a third impedance element, and a sensing impedance element arranged in a bridge configuration, the first impedance element having a variable impedance; a first input terminal coupled to the first impedance element and the second impedance element, the first input terminal configured to apply a stimulus signal to the impedance bridge; and a ground element positioned proximate to the sensing impedance element, the ground element configured to distort an electric field generated by the sensing impedance element in response to the stimulus signal toward the ground element.

Example 53 provides the sensor system according to example 52, where the ground element is one of a linear element, a half shell element, and a cylindrical element.

Example 54 provides the sensor system according to example 52 or 53, the sensor system further including circuitry to measure an impedance response within a given volume surrounding the sensing impedance element, the volume including a region of the electric field generated by the sensing impedance element having at least a threshold field strength.

Example 55 provides the sensor system according to any of examples 52 through 54, the sensor system further including a second ground element within the electric field, the second ground element configured to further distort the electric field toward the second ground element.

Example 56 provides the sensor system according to any of examples 52 through 55, where the sensing impedance element and the ground element are integrated in an electronic device, and the sensing impedance element and the ground element are arranged to direct the electric field in a direction pointing out of the device.

Example 57 provides a sensor system for measuring relative permittivity, the sensor system including an impedance bridge including a first impedance element, a second impedance element, a third impedance element, and a coupling network arranged in a bridge configuration, the first impedance element having a variable impedance, the impedance bridge further including a pair of input terminals and a pair of output terminals; a driver circuit to apply a stimulus signal to the impedance bridge, where the coupling network is couplable to an electrode pair to generate an electric field across the electrode in response to the applied stimulus signal and to sense an impedance response in an environment of the electrode pair; and circuitry configured to receive an output of the impedance bridge via the pair of output terminals, and measure a relative permittivity in the environment of the electrode pair based on the output of the impedance bridge.

Example 58 provides the sensor system according to example 57, where the circuitry is further configured to identify a material in the environment of the electrode pair based on the relative permittivity.

Example 59 provides the sensor system according to example 58, where the driver circuit is configured to generate a plurality of stimulus signals, where each stimulus signal is a sine wave having a respective frequency within a frequency range, and the circuitry is configured to identify the material in the environment of the electrode pair based on a variation in relative permittivities measured across the frequency range.

Example 60 provides the sensor system according to example 58 or 59, where the sensor system is embedded in a smart speaker configured to adjust an audio setting based on the identified material.

Example 61 provides the sensor system according to example 58 or 59, where the sensor system is embedded in a smartphone configured to adjust a behavior of the smartphone based on the identified material.

Example 62 provides the sensor system according to any of examples 59 through 61, where the circuitry is configured to identify the material using a classifier trained by impedance measurements of a plurality of detectable materials at a plurality of frequencies, where an output of the classifier identifies the material in the environment of the electrode pair.

Example 63 provides the sensor system according to example 62, where the classifier is trained by a plurality of arrangements of the plurality of detectable materials, and the circuitry is configured to identify a set of stacked materials using the classifier.

Example 64 provides a tissue sensor for classifying tissue, the sensor including an impedance bridge including a first impedance element, a second impedance element, a third impedance element, and a coupling network arranged in a bridge configuration, the impedance bridge further including a pair of input terminals and a pair of output terminals; a driver circuit to apply a stimulus signal to the impedance bridge, where the coupling network is couplable to an electrode pair to generate an electric field across the electrode in response to the applied stimulus signal and to sense an impedance response in an environment of the electrode pair; and circuitry configured to measure a relative permittivity in the environment of the electrode pair based on the output of the impedance bridge, and classify at least one tissue in the environment of the electrode pair based on the relative permittivity.

Example 65 provides the tissue sensor according to example 64, where the first impedance element is a variable impedance elements, and the circuitry is further configured to adjust the variable impedance element to balance an offset impedance on the electrode pair.

Example 66 provides the tissue sensor according to example 64 or 65, where the driver circuit is configured to apply a plurality of stimulus signals across a corresponding plurality of frequencies, and the circuitry is configured to measure relative permittivity as a function of frequency and classify the at least one tissue based on the relative permittivity as a function of frequency.

Example 67 provides the tissue sensor according to example 66, where the plurality of frequencies include frequencies in a range of 100 kHz to 1 MHz.

Example 68 provides the tissue sensor according to any of examples 64 through 67, where the circuitry is configured to classify the at least one tissue in the environment of the electrode pair as a cancerous tissue or a non-cancerous tissue.

Example 69 provides the tissue sensor according to any of examples 64 through 68, where the driver circuit includes an adjustable voltage source to generate a stimulus signal having an adjustable amplitude, the tissue sensor further including circuitry to adjust the amplitude of the stimulus signal according to a setting indicating a volume of tissue to be analyzed by the sensor.

Example 70 provides an earphone that includes an impedance bridge including a first impedance element, a second impedance element, a third impedance element, and a coupling network arranged in a bridge configuration, the coupling network couplable to at least one electrode, the impedance bridge further including an input terminal and a pair of output terminals; a driver circuit to apply a stimulus signal to the impedance bridge, where the at least one electrode is configured to sense an impedance response in an environment of the at least one electrode; and circuitry configured to receive an output of the impedance bridge via the pair of output terminals, determine a position of the earphone based on the output of the impedance bridge, and alter a behavior of the earphone based on the determined position of the earphone.

Example 71 provides the earphone according to example 70, where the circuitry is configured to determine whether the earphone is positioned within a user's ear, and the circuitry is configured to turn on an audio function of the earphone in response to determining that the earphone is positioned within the user's ear.

Example 72 provides the earphone according to example 70 or 71, where the circuitry is configured to determine whether the earphone is positioned within a user's ear, and the circuitry is configured to turn off an audio function of the earphone in response to determining that the earphone is not positioned within the user's ear.

Example 73 provides the earphone according to any of examples 70 through 72, where the first impedance element is a variable impedance element, the circuitry further configured to adjust the variable impedance element to balance an offset impedance on the at least one electrode.

Example 74 provides the earphone according to any of examples 70 through 73, the earphone further including at least one ground element positioned in an electric field generated by the at least one electrode and configured to distort the electric field in a direction away from the ground element.

OTHER IMPLEMENTATION NOTES, VARIATIONS, AND APPLICATIONS

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

In one example embodiment, any number of electrical circuits of the figures may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular arrangements of components. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more components. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of this Specification.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. Note that all optional features of the systems and methods described above may also be implemented with respect to the methods or systems described herein and specifics in the examples may be used anywhere in one or more embodiments.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph (f) of 35 U.S.C. Section 112 as it exists on the date of the filing hereof unless the words "means for" or "step for" are specifically used in the particular claims; and (b) does not intend, by any statement in the Specification, to limit this disclosure in any way that is not otherwise reflected in the appended claims.

What is claimed is:

1. A sensor system comprising:
    an impedance bridge comprising a first impedance element, a second impedance element, a third impedance element, and a coupling network arranged in a bridge configuration;
    a first input terminal coupled to the first impedance element and the second impedance element and configured to apply a first stimulus signal to the impedance bridge;
    a second input terminal coupled, in a first mode, to the coupling network and the third impedance element to apply a second stimulus signal to the impedance bridge; and
    at least one switch coupled to the second input terminal, the at least one switch controllable to decouple the second stimulus signal from the coupling network and the third impedance element in a second mode.

2. The sensor system of claim 1, wherein the coupling network comprises an electrode switch matrix couplable to a plurality of electrodes, the plurality of electrodes including at least two sensing electrodes.

3. The sensor system of claim 2, wherein in the first mode, the electrode switch matrix is coupled to a first sensing electrode and a second sensing electrode, and an output of the impedance bridge is correlated to a change in capacitance between the first sensing electrode and the second sensing electrode.

4. The sensor system of claim 2, wherein in the second mode, the electrode switch matrix is coupled to a particular sensing electrode of the at least two sensing electrodes, and an output of the impedance bridge is correlated to a change in an electric field in an environment of the particular sensing electrode.

5. The sensor system of claim 2, further comprising circuitry to select an electrode from the plurality of electrodes, and to instruct the electrode switch matrix to couple a terminal of the coupling network to a pin corresponding to the selected electrode.

6. The sensor system of claim 1, further comprising a driver circuit to apply the first stimulus signal to the first input terminal in the first mode.

7. The sensor system of claim 1, further comprising a driver circuit to apply, in the second mode, the first stimulus signal to the first input terminal and the second stimulus signal to the second input terminal, the second stimulus signal having opposite phase of the first stimulus signal.

8. The sensor system of claim 1, further comprising a driver circuit to generate a first stimulus waveform having a first frequency in the first mode, and to generate a second stimulus waveform having a second frequency in the second mode.

9. The sensor system of claim 1, wherein the first impedance element and the second impedance element are variable impedance elements.

10. The sensor system of claim 1, further comprising an amplifier circuit reconfigurable between the first mode and the second mode, the amplifier circuit includes, in the first mode,
    a first stage to convert a charge between a first output terminal and a second output terminal to a voltage, and
    a second stage to amplify a voltage difference between an output of the first stage and the first output terminal.

11. The sensor system of claim 1, further comprising an amplifier circuit reconfigurable between the first mode and the second mode, the amplifier circuit includes, in the second mode, at least one fully differential amplifier to amplify a voltage difference between a first output terminal of the impedance bridge and a second output terminal of the impedance bridge.

12. The sensor system of claim 1, further comprising,
    a driver circuit to generate the first stimulus signal and the second stimulus signal at a plurality of frequency settings, and
    circuitry to select one frequency setting of the plurality of frequency settings for the driver circuit.

13. The sensor system of claim 1, further comprising circuitry to select one of the first mode and the second mode.

14. The sensor system of claim 1, the sensor system further comprising,
    an amplifier circuit having a plurality of gain settings, and
    circuitry to select a gain setting for the amplifier circuit.

15. The sensor system of claim 1, further comprising circuitry to instruct the sensor system to obtain a sequence of measurements at a sequence of different sensor settings, wherein the different sensor settings comprise at least one of sensor mode, stimulus signal frequency, stimulus signal amplitude, and electrode selection.

16. A method comprising:
    receiving a first instruction to configure a sensor system in a first mode, the sensor system comprising a first impedance element, a second impedance element, a third impedance element, and a coupling network arranged in a bridge configuration;
    in response to the first instruction, coupling the coupling network to a first electrode and a second electrode;
    receiving a second instruction to configure the sensor system in a second mode; and in response to the second instruction, decoupling the coupling network from the second electrode.

17. The method of claim 16, further comprising,
in response to the first instruction, applying a first stimulus signal to a first input coupled to the first impedance element and the second impedance element, and applying a second stimulus signal to a second input coupled to the coupling network and the third impedance element; and in response to the second instruction, decoupling the second stimulus signal from the coupling network and the third impedance element.

18. The method of claim 17, further comprising applying a third stimulus signal to the first input in response to the second instruction, the third stimulus signal having a different frequency from the first stimulus signal.

19. The method of claim 16, further comprising adjusting an impedance setting of least one of the first impedance element and the second impedance element in response to the second instruction.

20. The method of claim 16, further comprising performing a calibration procedure that includes determining a first set of impedances for the first impedance element, the second impedance element, and the third impedance element based on a first offset impedance for the first mode, and determining a second set of impedances for the first impedance element, the second impedance element, and the third impedance element based on a second offset impedance for the second mode, wherein at least one of the second set of impedances is different from at least one of the first set of impedances.

* * * * *